(12) United States Patent
Talley et al.

(10) Patent No.: US 7,030,153 B2
(45) Date of Patent: Apr. 18, 2006

(54) 3,4-DIARYL THIOPHENES AND ANALOGS THEREOF HAVING USE AS ANTIINFLAMMATORY AGENTS

(75) Inventors: John J. Talley, Brentwood, MO (US); Stephen R. Bertenshaw, Brentwood, MO (US); Paul W. Collins, Deerfield, IL (US); Thomas D. Penning, Elmhurst, IL (US); David B. Reitz, Chesterfield, MO (US); Roland S. Rogers, Richmond Heights, MO (US)

(73) Assignee: G.D. Searle & Co., Chicago, IL (US)

( * ) Notice: Subject to any disclaimer, the term of this patent is extended or adjusted under 35 U.S.C. 154(b) by 112 days.

(21) Appl. No.: 10/329,332

(22) Filed: Dec. 27, 2002

(65) Prior Publication Data

US 2003/0153602 A1 Aug. 14, 2003

Related U.S. Application Data

(60) Division of application No. 09/711,737, filed on Nov. 13, 2000, now Pat. No. 6,599,934, which is a continuation of application No. 09/528,654, filed on Mar. 20, 2000, now abandoned, which is a continuation of application No. 09/366,484, filed on Aug. 3, 1999, now abandoned, which is a continuation of application No. 08/969,953, filed on Nov. 25, 1997, now abandoned, which is a continuation of application No. 08/464,722, filed on Jun. 27, 1995, now abandoned, which is a continuation-in-part of application No. 08/004,822, filed on Jan. 15, 1993, now abandoned.

(30) Foreign Application Priority Data

Jan. 14, 1994 (WO) .............................. PCT/US94/00466

(51) Int. Cl.
*A61K 31/38* (2006.01)
*C07D 333/16* (2006.01)

(52) U.S. Cl. .................................. 514/438; 549/78
(58) Field of Classification Search ................ 514/438; 549/78
See application file for complete search history.

(56) References Cited

U.S. PATENT DOCUMENTS

| | | | |
|---|---|---|---|
| 3,351,468 A | 11/1967 | Froehlich et al. | |
| 3,644,399 A | 2/1972 | Brown et al. | |
| 3,743,656 A | 7/1973 | Brown et al. | |
| 3,992,410 A | 11/1976 | Baird et al. | |
| 4,093,628 A | 6/1978 | Bagli et al. | |
| 4,108,867 A | 8/1978 | Baird et al. | |
| 4,267,184 A | 5/1981 | Cherkofsky | |
| 4,302,461 A | * 11/1981 | Cherkofsky | 514/445 |
| 4,321,118 A | 3/1982 | Felder et al. | |
| 4,381,311 A | 4/1983 | Haber | |
| 4,427,693 A | 1/1984 | Haber | |
| 4,432,974 A | 2/1984 | Haber | |
| 4,539,332 A | 9/1985 | Biftu et al. | |
| 4,585,789 A | 4/1986 | Okamoto et al. | |
| 4,590,205 A | 5/1986 | Haber | |
| 4,652,582 A | 3/1987 | Wilkerson | |
| 4,757,084 A | 7/1988 | Biftu | |
| 4,797,417 A | 1/1989 | Okamoto et al. | |
| 4,820,827 A | 4/1989 | Haber | |
| 4,853,473 A | 8/1989 | Fischer et al. | |
| 4,855,320 A | 8/1989 | Chatterjee et al. | |
| 4,929,525 A | 5/1990 | Kuroda et al. | |
| 4,968,817 A | 11/1990 | Brima | |
| 4,990,647 A | 2/1991 | Himmler et al. | |
| 5,094,681 A | 3/1992 | Kramer et al. | |
| 5,145,860 A | 9/1992 | Takasugi et al. | |
| 5,196,532 A | 3/1993 | Wuest et al. | |
| 5,207,817 A | 5/1993 | Karmer et al. | |
| 5,217,971 A | 6/1993 | Takasugi et al. | |
| 5,229,386 A | 7/1993 | Takasugi et al. | |
| 5,260,451 A | 11/1993 | Dannhardt et al. | |
| 5,274,072 A | 12/1993 | Weaver et al. | |
| 5,474,995 A | 12/1995 | Durcharme et al. | |
| 5,571,810 A | * 11/1996 | Matsuo et al. ........... | 514/231.5 |
| 5,710,140 A | 1/1998 | Durcharme et al. | |
| 6,239,173 B1 | 5/2001 | Wang et al. | |
| 6,274,590 B1 | 8/2001 | Talley et al. | |

FOREIGN PATENT DOCUMENTS

| | | |
|---|---|---|
| DE | 53075 | 6/1966 |
| EP | 0055470 A1 | 7/1982 |
| EP | 0087629 A2 | 9/1983 |

(Continued)

OTHER PUBLICATIONS

Ahluwalia, V.K., "Mechanism of the Debromination in Heterocyclization Using α, α–Dibromocarbonyl Compounds as Synthons," Synthetic Communications, 19(3&4), 619–626 (1989).

(Continued)

*Primary Examiner*—Deborah C. Lambkin
(74) *Attorney, Agent, or Firm*—Harness, Dickey & Pierce P.L.C.

(57) ABSTRACT

A class of 3,4-diaryl substituted thiophene, furan and pyrrole derivatives and analogs thereof, pharmaceutical compositions containing them and methods of using them to treat inflammation and inflammation-related disorders. Compounds of particular interest are defined by Formula I:

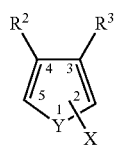

wherein Y is selected from O, S and $NR^1$; wherein $R^1$ is selected from hydrido and lower alkyl; wherein X is one or two substituent selected from hydrido, halo, lower alkoxycarbonyl and carboxyl; wherein $R^2$ and $R^3$ are independently aryl or heteroaryl; and wherein $R^2$ and $R^3$ are optionally substituted at a substitutable position with one or more radicals selected from sulfamyl, alkylsulfonyl, halo, lower alkoxy and lower alkyl; or a pharmaceutically-acceptable salt thereof.

32 Claims, No Drawings

FOREIGN PATENT DOCUMENTS

| | | |
|---|---|---|
| EP | 0087629 B1 | 9/1983 |
| EP | 0274867 A2 | 7/1988 |
| EP | 0300278 A2 | 1/1989 |
| EP | 0317845 A2 | 5/1989 |
| EP | 0397175 B1 | 11/1990 |
| EP | 0397175 A1 | 11/1990 |
| EP | 0407217 A1 | 1/1991 |
| EP | 0418845 A1 | 3/1991 |
| EP | 0418845 B1 | 3/1991 |
| EP | 0560407 B1 | 9/1993 |
| EP | 0560407 A1 | 9/1993 |
| EP | 0566175 A2 | 10/1993 |
| GB | 2000171 A | 1/1979 |
| JP | 48 91058 A | 11/1973 |
| JP | 48 91061 A | 11/1973 |
| JP | 50 121261 A | 9/1975 |
| JP | 63 68581 | 3/1988 |
| JP | 4-355767 A | 3/1991 |
| JP | 4 279672 A | 10/1992 |
| JP | 4 327583 A | 11/1992 |
| WO | WO 91/16055 A1 | 10/1991 |
| WO | WO 91/19708 A1 | 12/1991 |
| WO | WO 94/15932 A1 | 7/1994 |
| WO | WO 95/00501 A2 | 1/1995 |
| WO | WO 95/05376 A1 | 2/1995 |

OTHER PUBLICATIONS

Ahmed, et al., "Effect of the Double Bond Position on the Behaviour of Butenoides as Alkylating Agents," Revue Romaine de Chimie, pp. 79–82 (1993).

Ahmed, et al., "Effect of Position of the Double Bond on the Behaviour of Butenolides as Alkylating Agents," Egypt J. Chem. 33;No. 3, pp. 291–295 (1990).

Aslam et al., "Anhydrous Hydrogen Fluoride Catalyzed Friedel–Crafts Reactions of Thioaromatic Compounds," J. Org. Chem. 1991, 56, 5955–5958.

Basha et al., "A Mild, General Method for Conversion of Esters to Amides," Tetrahedron Letters, No. 48, pp. 4171–4174, 1977).

Capon et al., "Tautomerism of the Monohydroxy Derivatives of Five–Membered O, N, and S Heterocycles," J. Am. Chem. Soc. 1989 111, 5346–5356.

Chadwick et al., "Preparation of Thiophen Esters by the Hinsberg Reaction," J.C.S. Perkin I, (received Mar. 20, 1972), pp. 2079–2081 (1972).

Dann et al., "Desulfurization of 3,4–diphenylthiophene compounds with Raney nickel," Archiv der Pharmazie, Nr. 2, pp. 187–194 (1960) (with English abstract).

Dann et al., "3,4–diphenylthiophendicarbonsaure–(2.5)–bis–[(β–diathylamino)—athylestermethojodid], ein curareartiger, ruhepotentialstabilisierender Ester," Institut fur Angewandte Chemie er Universitat Eriangen–Numberg, pp. 135–145 (May 10, 1967).

Negishi et al., "Selective Carbon–Carbon Bond Formation via Transition Metal Catalysts . . . ," J. Org. Chem., vol. 42, No. 10, pp. 1821–1823 (1977).

Dikshit et al., "Synthesis and biological activity of 2,3– and 3,4–diarylfurans and 2,3,4–triaryl–2,5–dihydrofurane," Indian Journal of Chemistry, vol. 29B, pp. 954–960 (Oct. 1990).

Dinroth et al., "Uber Ungesaltigte heterocyclische Siebenringsyteme mit aromatischen Eigenschaften, I, Mitteil: Derivate des Aza–tropilidens," Jahrg, 89, pp. 2602–2607.

Doyama et al., "Carbonylation of Acetylenes under Water Gas Shift Conditions: A New Method for Synthesis of Furan–2(5H)–ones," J. Chem. Soc., Chem. Commun., 1, pp. 649–650 (1987).

Dunlop et al., "The Furans," Reinhold Publishing Corp., pp. 170–174 (1953).

Elderfield, R.C., "Heterocyclic Compounds," vol. 1, John Wesley, NY, pp. 177–179 and 184–189, (1956).

Ford et al., "The Preparation of (2(5H)–Furanones and Dyes Derived from Them," Jan. 1967, pp. 173–177.

Friedman, M., "Octaarylporphyrins," vol. 30, Mar. 1985, pp. 859–863.

Futaki et al., "NS–398, A Novel Non–Steroidal Anti–Inflammatory Drug with Potent Analgesic and Antipyretic Effects, which Causes Minimal Stomach Lesions," Gen Pharmac., vol. 24, No. 1, pp. 105–110, (1993).

Gans et al., "Anti–Inflammatory and Safety Profile of DuP 697, a Novel Orally Effective Prostaglandin Synthesis Inhibitor," J. Pharm. & Exper, Ther., vol. 254, pp. 180–187, (1990). (with abstract).

Gindy et al., "Phenylpropiolic Acids. Part XII. The Conversion of Phenylpropiolic Acids and their Esters into Thiophen Derivatives," J. Indian Chem. Soc., vol. LIII, pp. 490–495 (May 1976).

Girard et al., "Synthesis, Chemistry, and Photochemical Substitutions of 6, 11–Dihydro–5H–pyrrolo[2,1–b][3] benzazepin–11–ones," J. Org. Chem., pp. 3220–3224 (1983).

Hargreaves et al., "A new and sensitive method for measuring thermal nociception in cutaneous hyperalgesia," Pain, 32, pp. 77–88 (1988).

Hla et al., "Hyman cyclooxygenase–2 cDNA," Proc. Natl. Acad. Sci. USA, vol. 89, pp. 73847388 (1992).

Hornfeldt, A.B., "Tautomeric properties and some reactions of the 2–hydroxythiophene and the 2–hydroxyfuran systems," Svensk Kemish Tidskrift, vol. 80(10), pp. 343–357 (1968).

Joh et al., "Rhodium–Catalyzed Carbonylation of Acetylenes under Water–Gas Shift Reaction Conditions. Selective Synthesis of furan–2(5H)–ones," Organometallics, 10, pp. 2493–2498, (1991).

Kharasch et al., "Derivatives of Sulfuric Acids. V. 1–Fluorinate Sulfur Compounds," vol. 73, pp. 3240–3244, (Jul. 1951).

Kuo et al., "Synthesis and Antimicrobial Activity of Methyl 5–Nitro–3,4–diphenylfuran–2–carboxylate and Related Compounds," Chem. Pharm. Bull, No. 3, pp. 635–645 (1981).

Lai et al., "2,5b, 10b,11–Tetramethyldihydropyreno[5,6–c] Furan: The First Furan–Isoannelated[14]Annulene that Sustains as Strong a Diamagnetic Ring Current as the Parent System," Tetrahedron Letters, vol. 29, No. 8, pp. 3483–3486 (1988).

Lau et al., "Reductive Deoxygenation of Aryl Aldehydes and Ketones and Benzylic, Allylic, and Tertiary Alcohols by $ZnI_2$–NaCNBH3," J. Org. Chem., vol. 51, No. 15, pp. 3038–3043 (1986).

Lombardino et al., "Acidic–Antiinflammatory Agents—Correlations of Some Physical, Pharmacological and Clinical Data," Pfizer Central Research, Groton, Conn., pp. 1629–1635 (1975).

Masferrer et al., "Endogenous glucocorticoids regulate an inducible cyclooxygenase enzyme," Proc. Natl. Acad. Sci. USA, vol. 89, pp. 3918–3921 (1992).

Meade et al., "Differential Inhibition of Prostaglandin Endoperoxide Synthase (Cyclooxygenase) Isozymes by Aspirin and Other Non–steroidal Anti–inflammatory Drugs," J. Biol. Chem., 268 pp. 6610–6614 (1993).

Miyaura et al., "The Palladium–Catalyzed Cross–Coupling Reaction of Phenylboronic Acid with Haloarenes in the Presence of Bases," Synthetic Communications, 11(7), pp. 513–519 (1981).

Myers et al., "Antiinflammatory and/or Analgesic Diaryl 2–Substituted Thio) Furans," Research Disclosure, pp. 223–224 (May 1985).

Nakayama et al., "Preparation of 1–Phenylthio–1,3–Dienes by Reaction of 2,5–Dihydrothiophenes with Benzyne through Fragmentation of Sulfonium Ylide Intermediates," Tetrahedron Letters, vol. 30, No. 7, pp. 847–850, (1989).

Nakayama et al., "Regiochemistry of Thermal Extrusion and Sulfur from 2,6–Diaryl–1,4–Dithiine Yielding 2,5– and 3,4–Diarylthiophenes," Heterocycles, vol. 23, No. 8, pp. 1907–1910, (1985).

O'Banion et al., "cDNA cloning and functional activity of a glucocortocoid–regulated inflammatory cyclooxygenase," Proc. Natl. Acad. Sci., vol. 89, pp. 4888–4892, (Jun. 1992).

Otterness et al., "Laboratory Models for Testing Nonsteroidal Antiinflammatory Drugs," Nonsteroidal Antiinflammatory Drugs, ed. Joseph G. Lombardino, pp. 111–130 (1985).

Overberger et al., "Cyclic–Sulfones. II. The Polymerization of Styrene in the Presence of 3,4–Diphenylthiophene–1–dioxide and 3,4–Di–(p–chlorophenyl)–thiophene–1–dioxide," J. Amer. Chem. Soc. 72, pp. 4958–4961 (1950).

Rio et al., "Methyl 3,4–diphenylcyclopentadienone dicarboxylate addition reactions, photooxidation, 3,4–Diphenyl–2–furanone, 3,4–diphenyl–2–pyrrolinone and the corresponding dehydrodimers," Bulletin de la Societe Chimique de France, No. 9–10, pp. 1491–1495 (1976): (translation).

Schultze et al., "Zur Oxidation von 1,2–Thiazolen: Ein einfacher Zugang zu 1,2–Thiazol–3(2H)–on–1, 1–dioxiden," Helvetica chemica Acta, vol. 74, pp. 1059–1070 (1991).

Thiophenes, 27–Heterocycles, vol. 86, p. 449, (1977).

Pyrroles and other S–membered Rings, Chemical Abstracts, I. 67, 82089f and 82091a, (1967).

Toda et al., "A New Preparative Method for (E)–2, 3–Diarylbut–2–enedials," J. Chem. Soc., Chem. Commun., pp. 1234–1235 (1984).

Traverse, G. "Sul Comportamento Chimico di Taluni Intermedi Derivanti Dalla Idrolish Alcalina Perziale di Esteri Furan–β–Carbossilici," J. Farmaco. Ed. Sc. vol. XV, pp. 442–450. (May 1960).

Trieu et al., Zur Kondensation von β–Chlorvinylcarbonylverbindungen mit α–Mercaptocarbonduutrn, Zeitschrift fur Chemie, pp. 57–58, (1973).

Umernoto et al, "N–Fluoropyridinium Triflate and its Derivatives: Useful Fluorinating Agents," Tetrahedron Letters, vol. 27, No. 37, pp. 4465–4468, (1986).

Vijayaraghavan et al., "Synthesis of 3,4–Diaryl–2(5H)–furanones," Indian Journal of Chemistry, vol. 258, pp. 760–761 (Jul. 1986).

Vogtle et al., "Synthesen, Enantiomerentrennangen, Circulardichroismus, Racemislerungsschwelien, Runtgenstrukluranalysen und absolute Konformation neuer, gut zuganglicher Arenicene," Chem. Ber. Pp. 3112–3124 (1983).

Weisenfels et al., "β–Chlorvinylaldehyde nach dem Vilsmeier Prinzip," Z. Chem., pp. 471–472 (1966).

Wilkerson et al., "Antiinflammatory 4,5–Diarylpyrroles: Synthesis and QSAR,". J. Med. Chem. 37, pp. 988–998 (1994).

Wilkerson et al., "4,5–bis–(4–Fluorophenyl)–60 ,α–bis(trifluoromethyl)–2–furanmethane," Research Disclosure, pp. 221–222 (May 1985).

Wilkerson et al., "Antiinflammatory 2–Cyano–4,5–Diarylheterocycles," Research Disclosure, pp. 323–324 (Jun. 1986).

Winter et al., "Carrageenin–Induced Edema in Hind Paw of the Rat as an Assay for Antiinflammatory Drugs," P.S.E.B.M., pp. 544–547 (1962).

Wynberg et al. "The Mechanism of the Hinsberg Thiophene Ring Synthesis," J. Am. Chem. Soc. [87:8], pp. 1739–1742 (Apr. 20, 1965).

Yang et al., "3,4–Bis(tributylstannyl)furan: a Versatile building Block for the Regiospecific Synthesis of 3,4–Disubstituted Furans," J. Chem. Soc. Chem. Commun., pp. 656–658 (1992).

English language translation of Japanese Laid–Open Patent Application (Kokai) No. 4–279672 Inventor Hiroaki Iwasaki; filed Mar. 6, 1991 entitled "A Phenylenediamine–Based Compound and an Electrophotographic Photoreceptor Manufactured Using Said Compound."

* cited by examiner

3,4-DIARYL THIOPHENES AND ANALOGS THEREOF HAVING USE AS ANTIINFLAMMATORY AGENTS

CROSS-REFERENCE TO RELATED APPLICATIONS

This application is a divisional of U.S. application Ser. No. 09/711,737, filed Nov. 13, 2000, now U.S. Pat. No. 6,599,934, which is a continuation of application Ser. No. 09/528,654, filed Mar. 20, 2000, now abandoned, which is a continuation of application Ser. No. 09/366,484, filed Aug. 3, 1999, now abandoned, which is a continuation of application Ser. No. 08/969,953, filed Nov. 25, 1997, now abandoned, which is a continuation of application Ser. No. 08/464,722, filed Jun. 27, 1995, now abandoned, which is a continuation-in-part of application Ser. No. 08/004,822, filed Jan. 15, 1993, now abandoned.

This invention is in the field of antiinflammatory pharmaceutical agents and relates to compounds, compositions and methods for treating inflammation and inflammation-associated disorders, such as arthritis. This invention specifically relates to 3,4-diaryl substituted thiophene, furan and pyrrole derivatives and analogs thereof. More particularly, this invention relates to selected effective and safe compounds having antiinflammatory and/or analgesic activity without erosion of the stomach.

BACKGROUND OF THE INVENTION

Prostaglandins play a major role in the inflammation process, and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process, are also active in affecting other prostaglandin-regulated processes not associated with the inflammation process. Thus, use of high doses of most common NSAIDs can produce severe side effects, including life-threatening ulcers, that limit their therapeutic potential. An alternative to NSAIDs is the use of corticosteroids, which have even more drastic side effects, especially when long-term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci. USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci. USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Gen. Pharmac.*, 24, 105 (1993)) has reported that N-(2-cyclohexyloxy-4-nitrophenyl)methanesulfonamide is antiinflammatory and lacks gastric side effects.

The substituted thiophene compounds disclosed herein selectively inhibit cyclooxygenase II over cyclooxygenase I and relative the effects of inflammation. These compounds, in addition, do not display substantial inhibition of cyclooxygenase I and produce a reduced amount of side effects.

Selected symmetrical 3,4-bis(phenyl, naphthyl or substituted phenyl) thiophenes are known.

Preparation of a wide-variety of asymmetric biaryl compounds including substituted thiophene, furan and pyrrol heterocycles is described in U.S. Pat. No. 4,990,647 having a suggested utility as precursors for brighteners, pharmaceuticals, plant protection active compounds and liquid crystal materials.

U.S. Pat. No. 4,757,084 describes to Biftu analogs of 2,5-diaryl tetrahydrothiophenes having activity as PAF-antagonists which are said to be linked to physiological processes associated with a large group of diseases including inflammatory disease.

U.S. Pat. No. 5,196,532 to Wuest et al, describes 2,4-diaryl substituted thiophenes for cosmetics and the treatment of dermatological disorders.

U.S. Pat. No. 4,427,693 to Haber, describes antiinflammatory 4,5-diarylthiophene-2-methanamines. U.S. Pat. No. 4,432,974 to Haber, describes antiinflammatory and analgesic 2,3-diaryl-5-silylthiophenes. U.S. Pat. No. 4,302,461 to Cherkofsky, describes antiinflammatory 2,3-diarylthiophenes substituted with various alkyl sulfur radicals at position 5. U.S. Pat. No. 4,381,311 to Haber, describes antiinflammatory 4,5-diarylthiophene-2-methanols.

2,3-Diaryl-5-halo thiophenes are described in U.S. Pat. No. 4,590,205 to Haber, as analgesic or antiinflammatory agents. 4-Fluorophenyl and 4-methylsulfonylphenyl are among the various substituted phenyl groups that define the diaryl groups. U.S. Pat. No. 4,820,827 to Haber, describes 2,3-diaryl-5-bromo thiophenes, and specifically 5-bromo-2-(4-methylthiophenyl)-3-(4-fluorophenyl)thiophene, as having antiinflammatory and prostaglandin synthetase inhibitory activity for use in the treatment of inflammation and dysmenorrhea.

Japanese publication 4,335,767 describes photosensitive 3,4-bis(diazosubstitutedphenyl)thiophene pigments for use in photocopiers or facsimile receivers.

U.S. Pat. No. 3,743,656 to Brown et al, a CIP of U.S. Pat. No. 3,644,399, describes thiophene and furan derivatives having antiinflammatory activity, including ethyl 3,4-diphenylthiophene-2-propionate.

The above documents describing antiinflammatory activity show continuing efforts to find a safe and effective antiinflammatory agent.

DESCRIPTION OF THE INVENTION

A class of compounds useful in creating inflammation-related disorders is defined by Formula I:

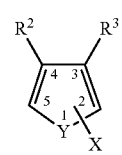

wherein Y is selected from S, O, and $NR^1$;
wherein $R^1$ is selected from hydride and $C_1$–$C_6$ alkyl;
wherein X is one or more substituents selected from
a) hydrido, halo, cyano, nitro, hydroxy, acyl, lower alkyl substituted at a substitutable position with a substituent selected from halo, hydroxyl, amino, acylamino, lower alkylamino, lower alkyl(acyl)amino, acyl, aryl optionally substituted with hydroxyl, a heterocyclic group, hydroxyimino and lower alkoxyimino, lower alkenyl optionally substituted at a substitutable position with cyano, amino optionally substituted at a substitutable position with a radical selected from acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (esterified carboxy)lower alkyl, N-containing heterocyclicsulfonyl, a heterocyclic group optionally substituted at a substitutable position with a substituent selected from the groups consisting of hydroxyl, oxo, amino and lower alkylamino, b) $S(O)_n R^5$, wherein $R^5$ is $C_1$–$C_6$ alkyl optionally substituted at a substitutable position with fluoro, and n is 0, 1 or 2, c) $C(R^6)(OR^8)(R^7)$ wherein $R^6$ and $R^7$ independently are selected from $CF_3$, $CF_2H$, $CFCl_2$, $CF_2Cl$, $CClFH$, $CCl_2F$, $CF_3CF_2$ and $C_1$–$C_2$ alkyl, and wherein $R^8$ is selected from hydrido, $C_1$–$C_4$ alkyl, $(C_1$–$C_3$ alkyl$)C(O)$ and $CO_2R^9$, wherein $R^9$ is $C_1$–$C_4$ alkyl, d) $C(O)ZR^4$, wherein Z is O, N, or S, and R4 is selected from hydrido, $C_1$–$C_6$ alkyl and aryl, and when Z is N then $R^4$ is independently taken twice, e) $C(R^9)(NHR^{11})(R^{10})$, wherein $R^9$ and $R^{10}$ are independently selected from $CF_3$, $CF_2H$, $CFCl_2$, $CF_2Cl$, $CClFH$ and $CCl_2H$, and $R^{11}$ is selected from hydrido and $C_1$–$C_3$ alkyl, and wherein $R^2$ and $R^3$ are independently selected from aryl or heteroaryl, wherein the aryl or heteroaryl radical is optionally substituted at a substitutable position with a radical selected from halo, lower alkyl, lower alkoxy, lower alkylthio, lower alkylsulfinyl, lower alkylsulfonyl, nitro, amide, amino, lower alkylamino, sulfamyl and lower alkylsulfonylamino;

provided that at least one of $R^2$ or $R^3$ is substituted with lower alkylsulfonyl or sulfamyl;

or a pharmaceutically-acceptable salt thereof.

Compounds of Formula I would be useful for the treatment of inflammation in a subject, and for treatment of other inflammation-associated disorders, for example, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erythematosus, osteoarthritis and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as antiinflammatory agents, such as for the treatment of arthritis, with the additional benefit of having significantly less harmful side effects.

The present invention also includes compounds which selectively inhibit cyclooxygenase II over cyclooxygenase I and do not significantly inhibit one or more other arachidonic pathway steps, such as thromboxane $B_2$ ($TXB_2$) production. Importantly, thromboxanes cause blood platelet aggregation and have vasoconstriction properties. Thus a lack of effect in the regulation of non-inflammation related thromboxane production is further evidence of the beneficial selectivity of the present compounds.

Preferably, the compounds of the present invention have a thromboxane $B_2$ inhibition $IC_{50}$ of greater than about 1.5 µM, as determined by a whole cell assay and preferably over 10 µM. The inhibition of the production of $TXB_2$ by a whole cell assay is a better indicator of potential in vivo behavior as the assay also incorporates such factors as cell transport.

More preferably, the compounds also have a selectivity ratio of cyclooxygenase II inhibition over cyclooxygenase I inhibition of at least 50 and preferably of at least 100. Such preferred selectivity may indicate an ability to reduce the incidence of common NSAID-induced side effects, such as ulcers.

The above mentioned aspects of the current invention exclude compounds such as 5-bromo-2-(4-methylthiophenyl)-3-(4-fluorophenyl)thiophene and N-(2-cyclohexyloxy-4-nitrophenyl)methanesulfonamide.

A preferred class of compounds consists of those compounds of Formula I wherein X is one or two substituents selected from hydrido, halo, cyano, nitro, hydroxyl, acyl, lower alkyl substituted at a substitutable position with a substituent selected from halo, hydroxyl, amino, acylamino, lower alkylamino, lower alkyl(acyl)amino, acyl, aryl optionally substituted with hydroxyl, a heterocyclic group, hydroxyimino and lower alkoxyimino, lower alkenyl optionally substituted at a substitutable position with cyano, amino optionally substituted at a substitutable position with a radical selected from acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (esterified carboxy)lower alkyl, N-containing heterocyclicsulfonyl, a heterocyclic group optionally substituted at a substitutable position with a substituent selected from the group consisting of hydroxyl, oxo, amino and lower alkylamino; and wherein $R^2$ and $R^3$ are independently selected from aryl and heteroaryl, wherein the aryl or heteroaryl radical is optionally substituted at a substitutable position with a radical selected from halo, lower alkyl, lower alkoxy, lower alkylthio, lower alkylsulfinyl, lower alkylsulfonyl, nitro, amino, amide, lower alkylamino, sulfamyl and lower alkylsulfonylamino; or a pharmaceutically-acceptable salt thereof, provided that at least one of $R^2$ or $R^3$ is substituted with lower alkylsulfonyl or sulfamyl.

A more preferred class of compounds consists of those compounds of Formula I wherein Y is S or O; wherein X is one or two substituents selected from hydrido, halo, cyano, nitro, hydroxyl, carboxy, lower alkoxycarbonyl, lower alkyl substituted at a substitutable position with a substituent selected from halo, hydroxyl, amino, acylamino, lower alkylamino, lower alkyl(acyl)amino, lower alkoxycarbonyl, carboxy, a heterocyclic group, hydroxyimino and lower alkoxyimino, lower alkenyl optionally substituted at a substitutable position with cyano, amino optionally substituted at a substitutable position with a radical selected from acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (alkoxycarbonyl)lower alkyl. N-containing heterocyclicsulfonyl, a heterocyclic group optionally substituted at a substitutable position with a substituent selected from the group consisting of hydroxyl, oxo, amino and lower alkylamino; and wherein $R^2$ and $R^3$ are independently selected from aryl and heteroaryl, wherein the aryl or heteroaryl radical is optionally substituted at a substitutable position with a radical selected from halo, lower alkyl, lower alkoxy, lower alkylthio, lower alkylsulfinyl, lower alkylsulfonyl, nitro, amino, amide, lower alkylamino, sulfamyl and lower alkylsulfonylamino; or a pharmaceutically-acceptable salt thereof, provided that at least one of $R^2$ or $R^3$ is substituted with lower alkylsulfonyl or sulfamyl.

A class of compounds of particular interest consists of those compounds of Formula I wherein X is one or two substituents selected from hydrido, fluoro, chloro, bromo and iodo; or a pharmaceutically-acceptable salt thereof.

A family of specific compounds of particular interest within Formula I consists of compounds and pharmaceutically-acceptable salts thereof as follows:
3-(4-methylsulfonylphenyl)-4-(4-fluorophenyl) thiophene;
4-(4-methylsulfonylphenyl)-3-(4-fluorophenyl)-2,5-dibromothiophene;
4-(4-methylsulfonylphenyl)-3-(4-fluorophenyl)-2-bromothiophene;
4-(4-methylsulfonylphenyl)-3-(4-fluorophenyl)-2,5-difluorothiophene;
4-(4-methylsulfonylphenyl)-3-(4-fluorophenyl)-2-fluorothiophene;
4-(4-methylsulfonylphenyl)-3-(4-fluorophenyl)-2,5-dichlorothiophene;
4-(4-methylsulfonylphenyl)-3-(4-fluorophenyl)-2-chlorothiophene;
ethyl[3-(4-methylsulfonylphenyl)-4-(4-fluorophenyl)thien-2-yl]carboxylate;
2-ethoxycarbonyl-4-(4-fluorophenyl)-3-(4-methanesulfonylphenyl)thienyl-5-carboxylic acid;
methyl[3-(4-methylsulfonylphenyl)-4-(4-fluorophenyl)thien-2-yl]carboxylate;
2-methoxycarbonyl-4-(4-fluorophenyl)-3-(4-methanesulfonylphenyl)thienyl-5-carboxylic acid;
4-(4-fluorophenyl)-3-(4-methanesulfonylphenyl) thienyl-2,5-dicarboxylic acid;
3-(4-methylsulfonylphenyl)-4-(4-chlorophenyl) thiophene;
4-(4-methylsulfonylphenyl)-3-(4-chlorophenyl)-2,5-dibromothiophene;
4-(4-methylsulfonylphenyl)-3-(4-chlorophenyl)-2-bromothiophene;
3-(4-methylsulfonylphenyl)-4-(4-bromophenyl)thiophene;
3-(4-methylsulfonylphenyl)-4-(4-methoxyphenyl) thiophene;
4-(4-methylsulfonylphenyl)-3-(4-methoxyphenyl)-2-bromothiophene;
3-(4-methylsulfonylphenyl)-4-(4-ethoxyphenyl) thiophene;
4-(4-methylsulfonylphenyl)-3-(4-ethoxyphenyl)-2-bromothiophene;
3-(4-methanesulfonylphenyl)-4-phenyl-thiophene;
4-(4-methylsulfonylphenyl)-3-phenyl-2,5-dibromothiophene;
4-(4-methylsulfonylphenyl)-3-phenyl-2-bromothiophene;
3-(4-methanesulfonylphenyl)-4-(4-methylphenyl) thiophene;
4-(4-methylsulfonylphenyl)-3-(4-methylphenyl)-2,5-dibromothiophene;
4-(4-methylsulfonylphenyl)-3-(4-methylphenyl)-2-bromothiophene;
3-(4-methylsulfonylphenyl)-4-(2-methyl-4-fluorophenyl) thiophene;
3,4-bis (4-methoxyphenyl)thiophene;
2-fluoro-5-[3-(4-methylsulfonylphenyl)thien-4-yl]pyridine;
2-methyl-5-[3-(4-methylsulfonylphenyl)thien-4-yl] pyridine;
2-chloro-5-[3-(4-methylsulfonylphenyl)thien-4-yl]pyridine;
5-[3-(4-methylsulfonylphenyl)thien-4-yl]pyridine;
2-methoxy-5-['-(4-methylsulfonylphenyl)thien-4-yl] pyridine;
2-fluoro-5-[3-(4-methylsulfonylphenyl)-3,5-dibromothien-4-yl]pyridine;
2-fluoro-5-[4-(4-methylsulfonylphenyl)-2-bromothien-3-yl] pyridine;
4-[4-(4-fluorophenyl)thien-3-yl]benzenesulfonamide;
4-[3-(4-fluorophenyl)-2,5-dibromo-thien-4-yl] benzenesulfonamide;
4-[3-(4-fluorophenyl)-2-bromo-thien-4-yl] benzenesulfonamide;
4-[4-(4-fluorophenyl)-2,5-difluoro-thien-3-yl] benzenesulfonamide;
4-[3-(4-fluorophenyl)-2-fluoro-thien-4-yl] benzenesulfonamide;
4-[4-(4-fluorophenyl)-2,5-dichloro-thien-3-yl] benzenesulfonamide;
4-[3-(4-fluorophenyl)-2-chloro-thien-4-yl] benzenesulfonamide;
4-[4-(4-fluorophenyl)-2-ethoxycarbonyl-thien-3-yl] benzenesulfonamide;
[4-(4-fluorophenyl)-2-ethoxycarbonyl-(4-aminosulfonylphenyl)thienyl]-5-carboxylic acid;
4-[4-(4-fluorophenyl)-2-methoxycarbonyl-thien-3-yl] benzenesulfonamide;
[4-(4-fluorophenyl)-2-methoxycarbonyl-(4-aminosulfonylphenyl)thienyl]-5-carboxylic acid;
[4-(4-fluorophenyl)-(4-aminosulfonylphenyl)thienyl]-2,5-dicarboxylic acid;
4-[4-(4-chlorophenyl)-thien-3-yl]benzenesulfonamide;
4-[3-(4-chlorophenyl)-2,5-dibromo-thien-4-yl] benzenesulfonamide;
4-[3-(4-chlorophenyl)-2-bromo-thien-4-yl] benzenesulfonamide;
4-[4-(4-bromophenyl)-thien-3-yl]benzenesulfonamide;
4-[4-(4-methoxyphenyl)-thien-3-yl]benzenesulfonamide;
4-[3-(4-methoxyphenyl)-2-bromo-thien-4-yl] benzenesulfonamide;
4-[4-(4-ethoxyphenyl)-thien-3-yl]benzenesulfonamide;
4-[3-(4-ethoxyphenyl)-2-bromo-thien-4-yl] benzenesulfonamide;
4-[phenyl-thien-3-yl]benzenesulfonamide;
4-[3-phenyl-2,5-dibromo-thien-4-yl]benzenesulfonamide;
4-[3-phenyl-2-bromo-thien-4-yl]benzenesulfonamide;
4-[4-(4-methylphenyl)-thien-3-yl]benzenesulfonamide;
4-[3-(4-methylphenyl)-2,5-dibromo-thien-4-yl] benzenesulfonamide;
4-[3-(4-methylphenyl)-2-bromo-thien-4-yl] benzenesulfonamide;
4-[4-(2-methyl-4-fluorophenyl)-thien-3-yl] benzenesulfonamide;
4-[4-(2-fluoropyridin-5-yl)-thien-3-yl]benzenesulfonamide;
4-[4-(2-methylpyridin-5-yl)-thien-3-yl] benzenesulfonamide;
4-[4-(2-chloropyridin-5-yl)-thien-3-yl]benzenesulfonamide;
4-[4-(pyridin-5-yl)-thien-3-yl]benzenesulfonamide;
4-[4-(2-methoxypyridin-5-yl)-thien-3-yl] benzenesulfonamide;
4-[4-(2-fluoropyridin-5-yl)-2,5-dibromo-thien-3-yl] benzenesulfonamide;

4-[4-(2-fluoropyridin-5-yl)-2-bromothien-3-yl]
benzenesulfonamide;
3-(4-fluorophenyl)-4-(methylsulfonylphenyl)furan;
4-(4-methylsulfonylphenyl)-3-(4-fluorophenyl)-2,5-dibromofuran;
4-(4-methylsulfonylphenyl)-3-(4-flurorphenyl)-2-bromofuran;
ethyl[3-(4-methylsulfonylphenyl)-4-(4-fluorophenyl) fur-2-yl]carboxylate;
2-ethoxycarbonyl-4-(4-fluorophenyl)-3-(4-methanesulfonylphenyl)thienyl-5-carboxylic acid;
methyl[3-(4-methylsulfonylphenyl)-4-(4-fluorophenyl) fur-2-yl]carboxylate;
2-methoxycarbonyl-4-(4-fluorophenyl)-3-(4-methanesulfonylphenyl)thienyl-5-carboxylic acid;
4-(4-fluorophenyl)-3-(4-methanesulfonylphenyl) thienyl-2,5-dicarboxylic acid;
3-(4-methylsulfonylphenyl)-4-(4-chlorophenyl)furan;
4-(4-methylsulfonylphenyl)-3-(4-chlorophenyl)-2,5-dibromofuran;
4-(4-methylsulfonylphenyl)-3-(4-chlorophenyl)-2-bromofuran;
4-(4-methylsulfonylphenyl)-3-(4-methoxyphenyl)furan;
4-(4-methylsulfonylphenyl)-3-(4-methoxyphenyl)-2-bromofuran;
3-(4-methylsulfonylphenyl)-4-(4-ethoxyphenyl)furan;
4-(4-methylsulfonylphenyl)-3-(4-ethoxyphenyl)-2-bromofuran;
3-(4-methanesulfonylphenyl)-4-phenyl-furan;
4-(4-methylsulfonylphenyl)-3-phenyl-2,5-dibromofuran;
4-(4-methylsulfonylphenyl)-3-phenyl-2-bromofuran;
3-(4-methanesulfonylphenyl)-4-(4-methylphenyl)furan;
4-(4-methylsulfonylphenyl)-3-(4-methylphenyl)-2,5-dibromofuran;
4-(4-methylsulfonylphenyl)-3-(4-methylphenyl)-2-bromofuran;
3-(4-methylsulfonylphenyl)-4-(2-methyl-4-fluorophenyl)furan;
2-fluoro-5-[3-(4-methylsulfonylphenyl)fur-4-yl]pyridine;
2-methyl-5-[3-(4-methylsulfonylphenyl)fur-4-yl]pyridine;
2-chloro-5-[3-(4-methylsulfonylphenyl)fur-4-yl]pyridine;
5-[3-(4-methylsulfonylphenyl)fur-4-yl]pyridine;
2-methoxy-5-[3-(4-methylsulfonylphenyl)fur-4-yl]pyridine;
2-fluoro-5-[3-(4-methylsulfonylphenyl)-2,5-dibromofur-4-yl]pyridine;
2-fluoro-5-[4-(4-methylsulfonylphenyl)-2-bromofur-3-yl] pyridine;
4-[4-(4-fluorophenyl)fur-3-yl]benzenesulfonamide;
4-[3-(4-fluorophenyl)-2,5-dibromo-fur-4-yl]
benzenesulfonamide;
4-[3-(4-fluorophenyl)-2-bromo-fur-4-yl]
benzenesulfonamide;
4-[4-(4-fluorophenyl)-2,5-difluoro-fur-3-yl]
benzenesulfonamide;
4-[3-(4-fluorophenyl)-2-fluoro-fur-4-yl]
benzenesulfonamide;
4-[4-(4-fluorophenyl)-2,5-dichloro-fur-3-yl]
benzenesulfonamide;
4-[3-(4-fluorophenyl)-2-chloro-fur-4-yl]
benzenesulfonamide;
4-[4-(4-fluorophenyl)-2-ethoxycarbonyl-fur-3-yl]
benzenesulfonamide;
4(4-fluorophenyl)-2-ethoxycarbonyl-(4-benzenesulfonamidyl)furyl-5-carboxylic acid;
4-[4-(4-fluorophenyl)-2-methoxycarbonyl-fur-3-yl]
benzenesulfonamide;
4-(4-fluorophenyl)-2-methoxycarbonyl-(4-benzenesulfonamidyl)furyl-5-carboxylic acid;
4-(4-fluorophenyl)-(4-benzenesulfonamidyl)furyl-2,5-dicarboxylic acid;
4-[4-(4-chlorophenyl)-fur-3-yl]benzenesulfonamide;
4-[3-(4-chlorophenyl)-2,5-dibromo-fur-4-yl]
benzenesulfonamide;
4-[3-(4-chlorophenyl)-2-bromo-fur-4-yl]
benzenesulfonamide;
4-[4-(4-bromophenyl)-fur-3-yl]benzenesulfonamide;
4-[4-(4-methoxyphenyl)-fur-3-yl]benzenesulfonamide;
4-[3-(4-methoxyphenyl)-2-bromo-fur-4-yl]
benzenesulfonamide;
4-[4-(4-ethoxyphenyl)-fur-3-yl]benzenesulfonamide;
4-[3-(4-ethoxyphenyl)-2-bromo-fur-4-yl]
benzenesulfonamide;
4-[4-phenyl-fur-3-yl]benzenesulfonamide;
4-[3-phenyl-2,5-dibromo-fur-4-yl]benzenesulfonamide;
4-[3-phenyl-2-bromo-fur-4-yl]benzenesulfonamide;
4-[4-(4-methylphenyl)-fur-3yl]benzenesulfonamide;
4-[3-(4-methylphenyl)-2,5-dibromo-fur-4-yl]
benzenesulfonamide;
4-[3-(4-methylphenyl)-2-bromo-fur-4-yl]
benzenesulfonamide;
4-[4-(2-methyl-4-fluorophenyl)-fur-3-yl]
benzenesulfonamide;
4-[4-(2-fluoropyridin-5-yl)-fur-3-yl]benzenesulfonamide;
4-[4-(2-methylpyridin-5-yl)-fur-3-yl]benzenesulfonamide;
4-[4-(2-chloropyridin-5-yl)-fur-3-yl]benzenesulfonamide;
4-[4(pyridin-5-yl)-fur-3-yl]benzenesulfonamide;
4-[4-(2-methoxypyridin-5-yl)-fur-3-yl]
benzenesulfonamide;
4-[4-(2-fluoropyridin-5-yl)-2,5-dibromo-fur-3-yl]
benzenesulfonamide; and
4-[4-(2-fluoropyridin-5-yl)-2-bromofur-3-yl]
benzenesulfonamide.

Within Formula I there is a subclass of compounds of high interest represented by Formula II:

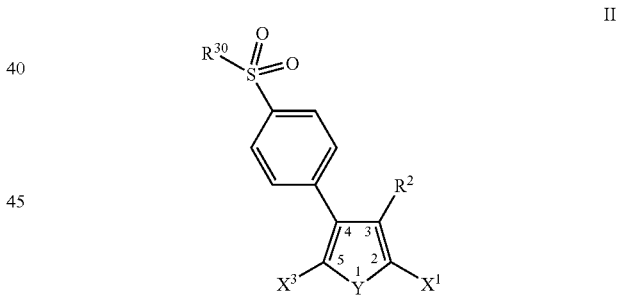

II wherein Y is selected from O, S and NR$^1$;

wherein R$^1$ is selected from hydrido and lower alkyl;

wherein X$^1$ and X$^2$ are independently selected from hydrido, halo, lower alkoxycarbonyl and carboxyl;

wherein R$^2$ is selected from aryl and heteroaryl; wherein R$^2$ is optionally substituted at a substitutable position with a radical selected from halo, lower alkoxy and lower alkyl; and wherein R$^{30}$ is selected from amino and lower alkyl, or a pharmaceutically-acceptable salt thereof.

A preferred class of compounds consists of those compounds of Formula II wherein Y is O or S;

wherein R$^2$ is selected from phenyl, naphthyl, biphenyl and pyridyl; wherein R$^2$ is optionally substituted at a substitutable position with a radical selected from halo, lower alkoxy and lower alkyl; and wherein $R^{30}$ is selected from amino and $C_1$–$C_3$ alkyl;
or a pharmaceutically-acceptable salt thereof.

A class of compounds of particular interest consists of those compounds of Formula II wherein $X^1$ and $X^2$ are independently selected from hydrido, fluoro, chloro, bromo, iodo, methoxycarbonyl, ethoxycarbonyl and carboxyl;

wherein $R^2$ is phenyl or pyridyl; wherein $R^2$ is optionally substituted at a substitutable position with a radical selected from fluoro, chloro, bromo, iodo, methoxy, ethoxy, methyl and ethyl; and wherein $R^{30}$ is amino or methyl;

or a pharmaceutically-acceptable salt thereof.

A family of specific compounds of particular interest within Formula II consists of compounds and pharmaceutically-acceptable salts thereof as follows:

4-(4-methylsulfonylphenyl)-3-(4-fluorophenyl) thiophene;
4-(4-methylsulfonylphenyl)-3-(4-fluorophenyl)-2,5-dibromothiophene;
4-(4-methylsulfonylphenyl)-3-(4-fluorophenyl)-2-bromothiophene;
ethyl[3-(4-methylsulfonylphenyl)-4-(4-fluorophenyl) thien-2-yl]carboxylate;
2-ethoxycarbonyl-4-(4-fluorophenyl)-3-(4-methylsulfonylphenyl)thienyl-5-carboxylic acid;
4-(4-fluorophenyl)-3-(4-methylsulfonylphenyl) thienyl-2,5-dicarboxylic acid;
4-(4-methylsulfonylphenyl)-3-(4-methoxyphenyl) thiophene;
4-(4-methylsulfonylphenyl)-3-(4-methoxyphenyl)-2-bromothiophene;
3-(4-methylsulfonylphenyl)-4-phenyl-thiophene;
3-(4-methylsulfonylphenyl)-4-(4-methylphenyl) thiophene;
3-(4-methylsulfonylphenyl)-4-(2-methyl-4-fluorophenyl) thiophene;
2-fluoro-5-[3-(4-methylsulfonylphenyl) thien-4-yl]pyridine;
4-[4-(4-fluorophenyl)thien-3-yl]benzenesulfonamide;
4-[3-(4-fluorophenyl)-2,5-dibromo-thien-4-yl] benzenesulfonamide;
4-[3-(4-fluorophenyl)-2-bromo-thien-4-yl] benzenesulfonamide; and
3-(4-fluorophenyl)-4-(methylsulfonylphenyl)furan.

When the term "alkyl" is used, either alone or within other terms such as "haloalkyl", "alkylamine" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl, octyl and the like. Where the term "alkenyl" is used, it embraces linear or branched radicals having two to about twenty carbon atoms or, preferably, two to about twelve carbon atoms. More preferred alkenyl radicals are "lower alkyl" radicals having two to about six carbon atoms. Suitable "lower alkenyl" may be a straight or branched one such as vinyl, allyl, isopropenyl, propenyl, butenyl, pentenyl or the like, in which preferably one is isopropenyl. Said lower alkenyl may be substituted with cyano. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine atoms. The terms "halo lower alkyl" and "lower alkyl substituted with halo" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. The terms "hydroxyalkyl" and "lower alkyl substituted with hydroxyl" embraces linear or branched alkyl radicals having one to about ten carbon atoms any one of which may be substituted with one or more hydroxyl radicals. The terms "lower alkoxy" and "lower alkoxyalkyl" embrace linear or branched oxy-containing radicals each having alkyl portions of one to about six carbon atoms, such as methoxy radical. The term "lower alkoxyalkyl" also embraces alkyl radicals having two or more alkoxy radicals attached to the alkyl radical, that is, to form monoalkoxyalkyl and dialkoxyalkyl radicals. The "lower alkoxy" or "lower alkoxyalkyl" radicals may be further substituted with one or more halo atoms, such as fluoro, chloro or bromo, to provide "haloalkoxy" or "haloalkoxyalkyl" radicals. Examples of "alkoxy" radicals include methoxy, ethoxy, propoxy, isopropoxy, butoxy and trifluoromethoxy. The term "aryl", alone or in combination, means a carbocyclic aromatic system containing one, two or three rings herein such rings may be attached together in a pendent manner or may be fused. The term "aryl" embraces aromatic radicals such as phenyl, naphthyl, phenyl substituted with lower alkyl [e.g. tolyl, xylyl, mesityl, cumenyl, di(tert-butyl)phenyl, etc.] and the like, in which the preferable one is phenylnaphthyl, tetrahydronapthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic group containing 1 to 4 nitrogen atoms [e.g. pyrrolindinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, furyl, etc.; unsaturated 3- to 6-membered heteromonocyclic group containing 1 to 2 oxygen atoms and 1 to 3 nitrogen atoms, for example, oxazolyl, isoxazolyl, oxidiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl as exemplified above, hydroxy, oxo, amino and lower alkylamino. Preferably one is lower alkyl substituted with a heterocyclic group for $R^1$ is pyrrolidinylmethyl. Preferable one in a heterocyclic group optionally substituted with substituent(s) selected from the group consisting of hydroxy, oxo, amino and lower alkylamino for $R^1$ if 4-hydroxy-2,5-dioxo-3-pyrrolin-3-yl, 2-aminothiazol-4-yl or 2-methylaminothizol-4-yl. The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl", "sulfamoyl" or "sulfonamidyl" denote a sulfonyl radical substituted with an amine radical, forming a sulfonamide (—$SO_2NH_2$). Suitable "sulfamoyl substituted with lower alkyl" may be methylsulfamoyl, ethylsulfamoyl, isopropylsulfamoyl, dimethylsulfamoyl, diethylsulfamoyl and the like, in which preferably one is methylsulfamoyl or dimethylsulfamoyl. The term "acyl", whether used alone, or within a term such as "acylamino", denotes a radical provided by the residue after removal of hydroxyl from an organic acid. Suitable "acyl" and acyl moiety in the terms "acylamino" and "lower alkyl(acyl)amino" may be carboxy; esterified carboxy; carbamoyl optionally substituted with substituent(s) selected from the group consisting of lower alkyl, halo(lower) alkyl, aryl, hydroxy, lower alkylamino(lower) alkyl, a heterocyclic group (esterified carboxy)lower alkyl and carboxy(lower) alkyl [e.g. lower alkyl-carbamoyl; aryl-carbamoyl; carbamoyl substituted with a heterocyclic group, (esterified carboxy) lower alkyl or carboxy(lower)alkyl; lower alkyl-carbamoyl substituted with hydroxy, lower alkylamino, (esterified carboxy)lower alkyl or carboxy(lower)alkyl; etc.]; lower alkanoyl; aroyl; a heterocicarbonyl and the like. The term "acylamino" embraces an amino radical substituted with an acyl group. An example of an "acylamino" radical is acetylamino: ($CH_3C(=O)$—NH—). The terms "carboxy" or "carboxyl", whether used alone or with other terms, such as "carboxyalkyl", denotes —$CO_2H$. The term "carboxyalkyl" embraces radicals having a carboxy radical as defined above, attached to an alkyl radical. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl (C=O) radical. Examples of such "alkoxycarbonyl" ester radicals include ($CH_3$)$_3$CO—C(=O)— and —(O=)C—$OCH_3$. The terms "alkoxycarbonylalkyl" and "esterified carboxylower alkyl" embraces radicals having "alkoxycarbonyl", as defined above substituted to an alkyl radical. Examples of such esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethyoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like. The lower alkyl-carbamoyl may be substituted with halo or an unsubstituted one such as methylcarbamoyl, ethylcarbamoyl, propylcarbamoyl, dimethylcarbamoyl, 2,2,2-trifluoroethylcarbamoyl or the like. The aryl-carbamoyl may be phenylcarbamoyl, naphthylcarbamoyl, tolylcarbamoyl, xylylcarbamoyl, mesitylcarbamoyl, cumenylcarbamoyl, and the like, in which the preferable one is phenylcarbamoyl. The carbamoyl substituted with a heterocyclic group may be one substituted with a heterocyclic group as mentioned above, in which preferably one is tetrazolylcarbamoyl. The carbamoyl substituted with (esterified carboxy) lower alkyl may be methoxycarbonylmethylcarbamoyl, methoxycarbonylethylcarbamoyl, ethoxycarbonylmethylcarbamoyl, ethoxycarbonylethylcarbamoyl, benzyloxycarbonylmethylcarbamoyl and the like. The carbamoyl substituted with carboxy(lower)alkyl may be carboxymethylcarbamoyl, carboxyethylcarbamoyl and the like. The lower alkycarbamoyl substituted with hydroxyl may be N-hydroxy-N-methylcarbamoyl, N-ethyl-N-hydroxycarbamoyl, N-hydroxy-N-propylcarbamoyl, N-hydroxy-N-isopropylcarbamoyl and the like, in which the preferable one is N-hydroxy-N-methylcarbamoyl. The lower alkylcarbamoyl substituted with lower alkylamino may be methylaminomethylcarbamoyl, dimethylaminomethylcarbamoyl, dimethylaminoethylcarbamoyl, diethylaminoethylcarbamoyl, isopropylaminomethylcarbamoyl, isopropylaminoisobutylcarbamoyl and the like, in which the preferable one is dimethylaminoethylcarbamoyl. The lower alkylcarbamoyl substituted with (esterified carboxy)lower alkyl may be (methoxycarbonylmethyl)-ethylcarbamoyl, (ethoxycarbonylmethy)methylcarbamoyl, (benzyloxcarbonylmethyl)methylcarbamoyl, (benzyloxycarbonylethyl) ethylcarbamoyl and the like, in which preferably one is (ethoxycarbonylmethyl) methylcarbamoyl. The lower alkylcarbamoyl substituted with carboxy(lower)alkyl may be (carboxymethyl) ethylcarbamoyl, (carboxyethyl)ethylcarbamoyl and the like, in which the preferable one is (carboxymethyl) methylcarbamoyl. The lower alkanoyl may be a substituted or unsubstituted one such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The arcyl may be benzoyl, naphthoyl, toluoyl, di(tert-butyl)benzoyl and the like and the aryl in said aroyl may be substituted with hydroxyl. The heterocyclic moiety in the term "a heterocliccarbonyl" may be one mentioned above as a heterocyclic group and preferably one in said heterocliccarbonyl is morpholinocarbonyl, pyrrolidinylcarbonyl or methylpiperazinylcarbonyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "alkylthio" embraces radicals containing a linear or branched alkyl radical, of one to ten carbon atoms, attached to a divalent sulfur atom. An example of "alkylthio" is methylthio, ($CH_3$—S—). The term "alkylsulfinyl" embraces radicals containing a linear or branched alkyl radical, of one to ten carbon atoms, attached to a divalent —S(=O)— atom. The terms "N-alkylamino" and "N,N-dialkylamino" denote amino groups which have been substituted with one alkyl radical and with two alkyl radicals, respectively. Suitable "lower alkylamino" may be mono or di(lower alkyl)amino such as methylamino, ethylamino, dimethylamino, diethylamino or the like. The term "imino" in "hydroxyimino" and "alkoxyimino" denotes a —C=N— radical. The term "hydroxyimino" denotes a —C=N—OH radical. The term "amide" denotes a radical formed by an amino substituted carbonyl, or —C(=O)—$NH_2$.

The present invention comprises a pharmaceutical composition comprising a therapeutically-effective amount of a compound of Formula I as defined above but without excluding compounds defined in the overall proviso that $R^2$ and $R^3$ are not at same time 1) para-hydroxyphenyl, 2) para-methoxyphenyl, 3) para-acetoxyphenyl, 4) para-chlorophenyl, 5) para-methylphenyl or 6) para-bromophenyl, but preferably of Formula I, in association with at least one pharmaceutically-acceptable carrier, adjuvant or diluent.

The present invention also comprises a method of treating inflammation or inflammation-related disorders in a subject, the method comprising administering to a subject having such inflammation or disorder, a therapeutically-effective amount of a compound of Formula I, as defined above but without excluding compounds defined in the overall proviso that $R^2$ and $R^3$ are not at same time 1) para-hydroxyphenyl, 2) para-methoxyphenyl, 3) para-acetoxyphenyl, 4) para-chlorophenyl, 5) para-methylphenyl or 6) para-bromophenyl, but preferably of Formula I in unit dosage form.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–XIII, wherein the $R^1$–$R^3$ substituents are as defined for Formula I, above, except where further noted.

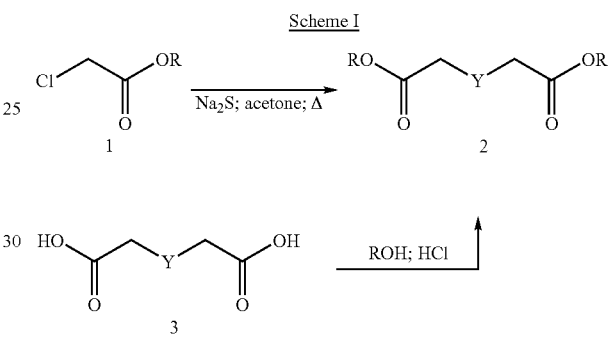

Scheme I

Synthetic Scheme I shows the preparation of dialkylester 2 from starting ester 1 or diacid 3 where R is lower alkyl. The dialkylester 2 can be prepared by the condensation of alkyl chloroacetate 1 with sodium sulfide nonahydrate, where Y is sulfur. Alternatively, dialkylester 2 can be formed by alcohol esterification of diacid 3.

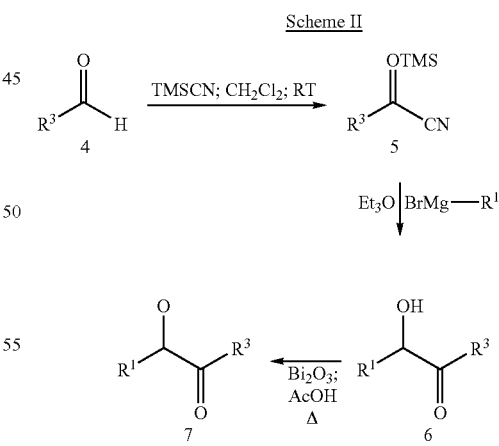

Scheme II

Synthetic Scheme II shows the preparation of diones 7 in three steps from commercially available aldehydes. In Step 1, treatment with trimethylsilyl cyanide (TMSCN) provides the trimethylsiloxy nitrile 5. In Step 2, the nitrile 5 is treated with a Grignard reagent to form the hydroxy ketone 6. In Step 3, the hydroxy ketone 6 is oxidized to give the desired diketone 7.

Scheme III

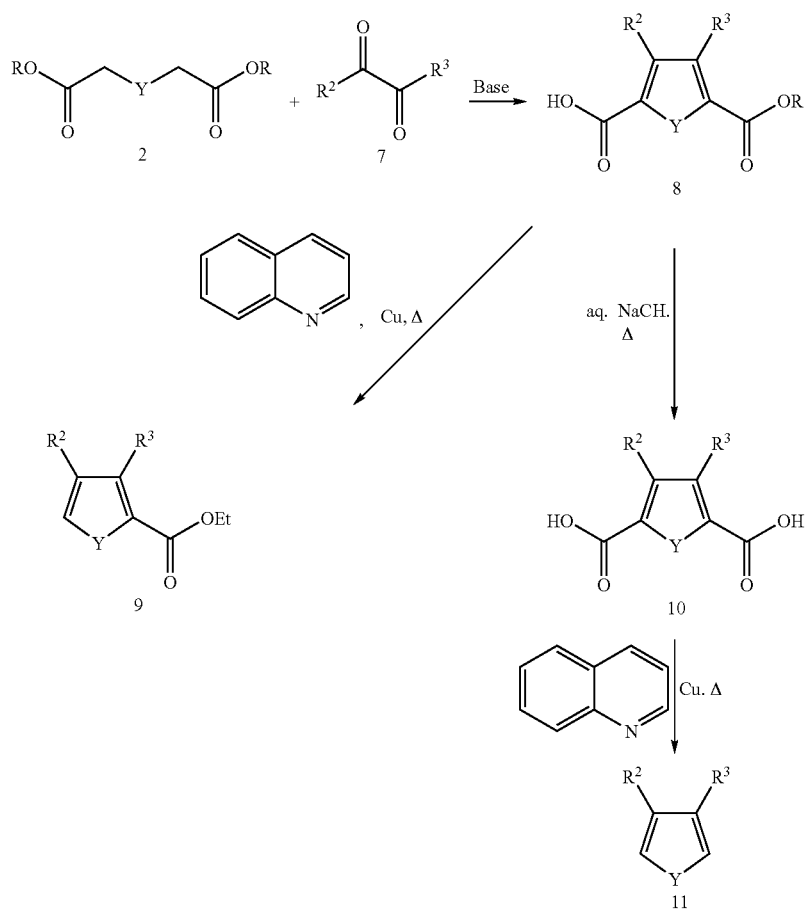

Synthetic Scheme III shows the preparation of half ester 8, monoester 9, diacid 10 and 3,4-substituted heterocycles 11 of the present invention. In Step 1, the half ester 8 is formed by the Hinsberg condensation of dialkyl ester 2 and diketone 7, prepared in Synthetic Schemes I–II, respectively, by treatment with base, such as sodium methoxide or potassium tert-butoxide, in solvents, such as THF or alcohols. The half ester 8 can be isolated, or saponified in Step 2 to the yield diacid 10. See D. J. Chadwick et al, *J. Chem. Soc. Perkin I*, 2079 (1972). Alternatively, a procedure analogous to that described in Overberger et al, *J. Amer. Chem. Soc.*, 72, 4958 (1950), can be used to prepare the diacid 10. In step 3, the diacid 10 is decarboxylated through the addition of copper powder, quinoline and heat to form the antiinflammatory 3,4-substituted heterocycle 11 in a process essentially analogous to that described in D. J. Chadwick et al, *J. Chem. Soc. Perkin I,* 2079 (1972). Alternatively, the half ester 8 can be monodecarboxylated to the ester 9 by a method similar to that described in Step 3, above.

Scheme IV

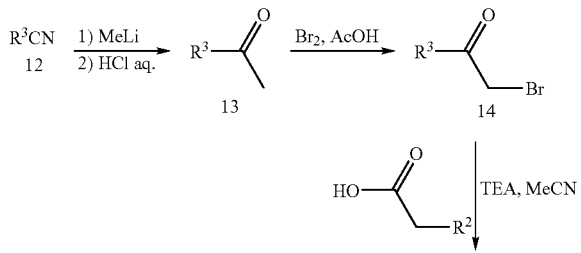

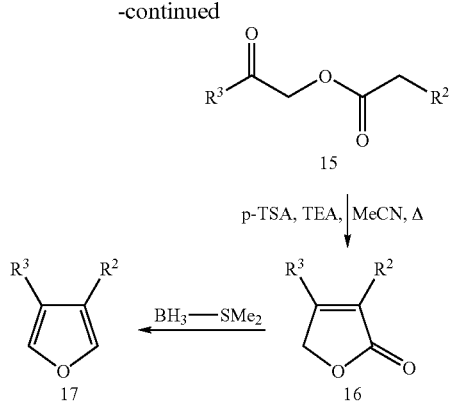

Synthetic Scheme IV shows the five step preparation of 3,4-substituted furans 17 from the nitrile 12. In step 1, reaction of the nitrile 12 with an alkyl lithium, such as methyl lithium, at −78° C., is followed by acidification to give the ketone 13. In step 2, the ketone 13 is brominated to yield the bromoketone 14. In step 3, bromoketone 14 is coupled with an acid to produce the ester 15. In step 4, cyclization of the ester 15 by reflux with p-toluenesulfonic acid and triethylamine produces the furanone 16. In step 5, furanone 16 is reduced with borane dimethylsulfide complex to give the antiinflammatory furans 17 of the present invention.

Scheme V

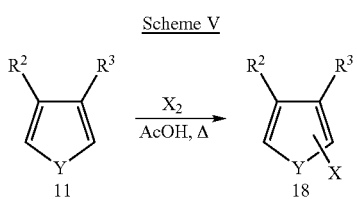

The compounds of the present invention wherein X is bromo or chloro, are prepared by treating the decarboxylation product heterocycle 11 or 17, prepared in Synthetic Scheme III or IV, with Br$_2$ or Cl$_2$, respectively. In other words Cl$_2$ or Br$_2$ may be used to yield monohalo or dihalo heterocycle 18 as in the above Scheme V.

Scheme VI

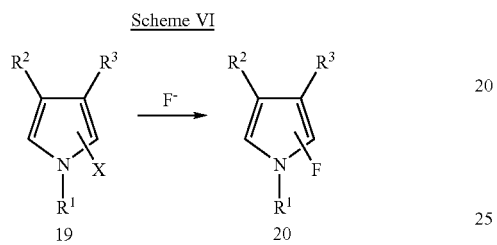

The compounds of Formula I, wherein Y is NR$^1$ and X is chloro or bromo, may be treated with silver fluoride or potassium fluoride to obtain compound 20 of Formula I wherein Y is NR$^1$ and X is fluoro. This preparation shown in Scheme VI is analogous to that described in U.S. Pat. No. 4,652,582.

Scheme VII

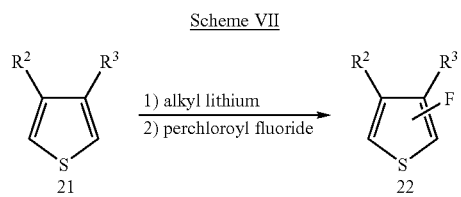

Compound 21 of Formula I, wherein Y is S and X is H, may be treated in two steps, first with alkyllithium and then with perchloryl fluoride, to obtain compound 22 of Formula I, wherein X is fluoro, in the manner set forth in the Scheme VII using methods analogous to those set forth in U.S. Pat. No. 4,590,205.

Scheme VIII

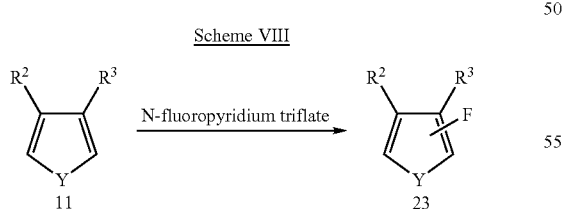

Alternatively, compounds of Formula I, wherein Y is O or S and X is hydrogen, may be treated with N-fluoropyridinium triflate as set forth in the Scheme VIII using methods analogous to those described in *Tetrahedron Letters*, 27, 4465 (1986).

Alternatively, heterocycle 11 may be substituted at the 2 and 5 position by methods outlined for each of these substituents in their respective patent application and/or Patents, i.e. PCT Publication WO 91/19708, U.S. Pat. Nos. 4,590,205, 4,302,461, 4,427,693 and 4,432,974.

Scheme IX

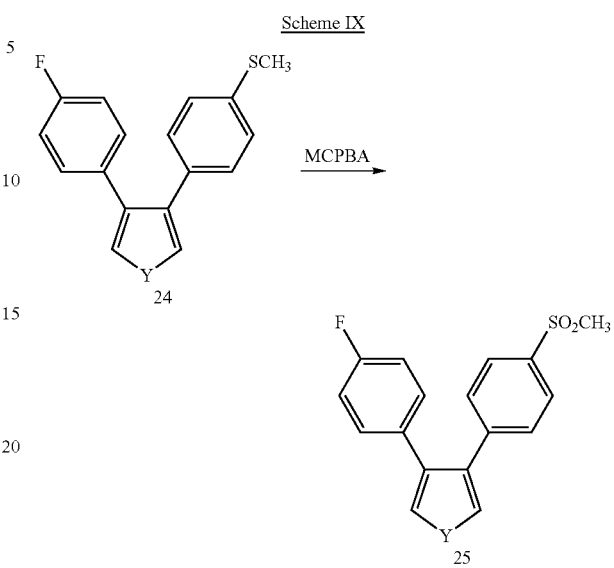

Compounds of Formula I wherein R$^3$ is alkylthiophenyl, may be treated with m-chloroperoxybenzoic acid (MCPBA) to obtain other compounds of Formula I, wherein R$^3$ is alkylsulfonylphenyl, in the manner set forth in Scheme IX.

Scheme X

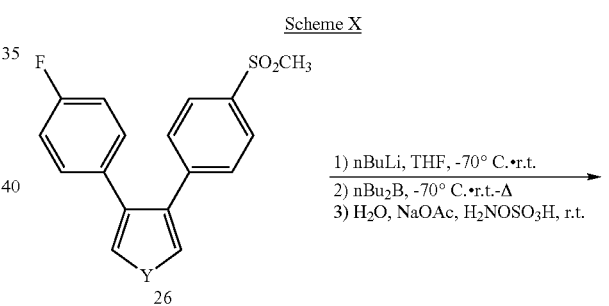

Compounds of Formula I wherein R$^3$ is alkylsulfonylphenyl, may be treated in three steps to obtain other compounds of Formula I, wherein R$^3$ is benzenesulfonamide, in the manner set forth in Scheme X. In Step 1, the alkylsulfone is treated at –70° C. with n-butyllithium. In step 2, tri-n-butyl borane in THF is added and refluxed overnight. After cooling to room temperature, water, sodium acetate and hydroxylamine-O-sulfonic acid are added to form the sulfonamide.

Scheme XI

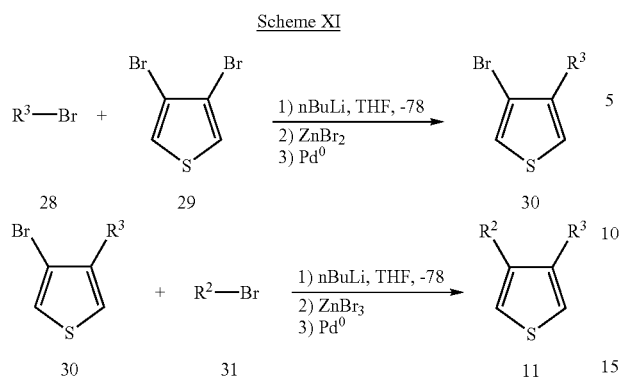

Synthetic Scheme XI shows the two step preparation of 3,4-disubstituted heterocyclic antiinflammatory agents 11 from 1,2-dibromo-thiophene 29 and the available bromides 28 and 31. In step one, halogen-metal interchange of 28 with n-butyllithium in THF at −78° C. gives the 3-lithiocompounds which subsequently react with zinc chloride to give the corresponding zinc reagents. Negishi coupling [Negishi et al, *J. Org. Chem.*, 42, 1821 (1977)] of the zinc reagents with 29 gives the monocoupled thiophene bromides 30. In step two, this process is repeated with bromides 31 to yield the 3,4-disubstituted heterocyclic antiinflammatory agents 11.

Scheme XII

Synthetic Scheme XII shows the two step procedure for the preparation of 3,4-disubstituted heterocyclic antiinflammatory agents 11 from monocoupled thiophene bromides 30 (prepared in Synthetic Scheme XI) and substituted boronic acids 33 using a sequential coupling procedure which is similar to the coupling procedure developed by Suzuki, et al., [*Syn. Commun.*, 11, 513 (1981)]. In step one, halogen-metal interchange of the bromides 31 in THF at −78° C. generates the corresponding organolithium reagents which are reacted with trimethyl borate. Hydrolysis with hydrochloric acid provides the substituted boronic acids 33. In step two, the monocoupled bromides 30 (prepared in Synthetic Scheme XI) are coupled in toluene at reflux in the presence of Pd° catalyst, e.g., tetrakis(triphenylphosphine) palladium (0), and 2M sodium carbonate, with 33 to give the 3,4-disubstituted heterocyclic antiinflammatory agents 11 of this invention.

Scheme XIII

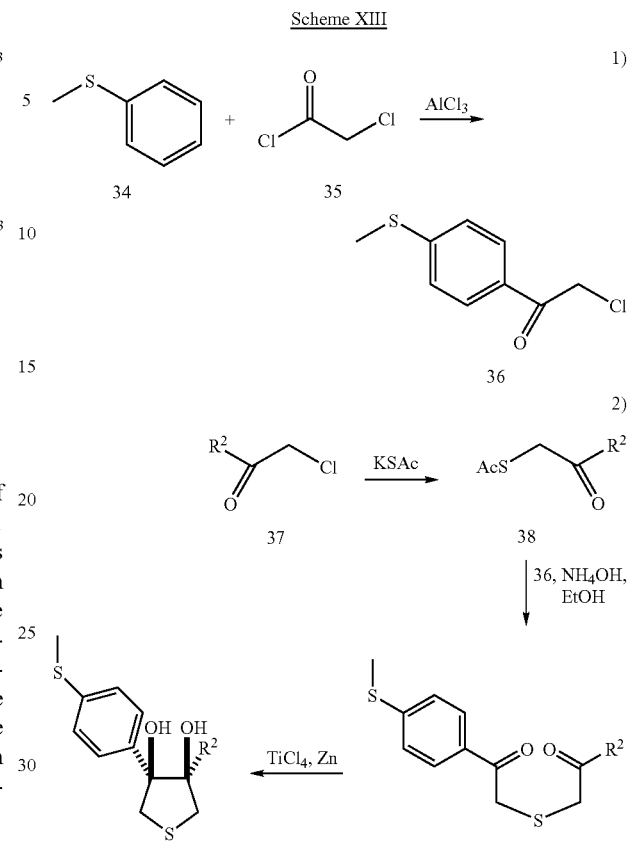

Alternatively, the heterocycles of the present invention, where Y is sulfur and $R^3$ is 4-methylsulfonyl, may be prepared essentially as the McMurray synthesis, as shown in Scheme XIII. In Step 1, thioanisole 34 is acetylated with chloroacetyl 35 in the presence of $AlCl_3$ to form the haloacetophenone 36. In Step 2, the thioacetylketone 38 is prepared by the treatment of ketone 37 with potassium thioacetate in ethanol. In Step 3, intermediates 36 and 38 are coupled to form the dione 39 in the presence of ammonium hydroxide. In Step 4, diol 40 is formed through the treatment of dione 39 with $TiCl_4$ and zinc dust. Thiophene 41 is formed in Step 5 by refluxing diol 40 with p-toluenesulfonic acid in toluene. The antiinflammatory (4-methylsulfonylphenyl) thiophenes 42 of the invention are formed through the oxidation of the alkylthiophenyl thiophene 41 with meta-chloroperoxybenzoic acid in dichloromethane.

An alternate procedure utilized in the present invention is essentially analagous to that outlined by H. Wynberg and H. J. Kooreman, *J. Am. Chem. Soc.*, 87, 1739 (1985).

The following examples contain detailed descriptions of the methods of preparation of compounds of Formula I–II. These detailed descriptions fall within the scope, and serve to exemplify the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

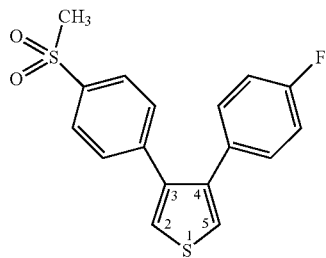

3-(4-Methylsulfonylphenyl)-4-(4-fluorophenyl) thiophene

Step 1: Preparation of Dimethyl Thiodiglycolate

A 2L, 4-neck round bottom flask equipped with a mechanical stirrer was charged with thiodiglycolic acid (300.3 g, 2 mol) and methanol (810 ml). Anhydrous HCl was then bubbled through this solution with stirring for 0.5 hours. Stirring was continued for an additional 16 hours at 27° C. at which time the methanol was removed by distillation at reduced pressure. The residue was dissolved in diethyl ether and washed with brine (300 ml), twice with saturated bicarbonate (2×500 ml) and brine (500 ml). The diethyl ether was dried with $Na_2SO_4$ and the solvent removed by distillation at reduced pressure. Vacuum distillation of the resulting residue yielded 229.7 g (1.29 mol, 64%) of dimethyl thiodiglycolate; $^1$H NMR ($CDCl_3$) δ3.37 (s, 4H), 3.72 (s, 6H).

Step 2: Preparation of 2-methoxycarbonyl-3-(4'-fluorophenyl)-4-(4'-methylthiophenyl)-thienyl-5-carboxylic acid and 2-methoxycarbonyl-3-(4'-methylthiophenyl)-4-(4'-fluorophenyl)-thienyl-5-carboxylic acid.

To a stirred solution of 4-fluoro-4'-methylthio benzil (33.34 g, 122 mmol) and dimethyl thiodiglycolate (43.4 g, 244 mmol) from Step 1 in tetrahydrofuran (THF) (400 ml) at ambient temperature was added 25% NaOMe in methanol solution (83.7 ml, 366 mmol). This solution was immediately warmed to 65° C. and stirred for 2.5 hours. The reaction mixture was cooled to room temperature and poured into 1L of 3M $NH_4OH$ and 1L diethyl ether, shaken, and separated. The aqueous layer was acidified with concentrated HCl, saturated with NaCl, and extracted with 1L ethyl acetate. The ethyl acetate was dried over $Na_2SO_4$ and concentrated in vacuo to provide 73.43 g of crude intermediate as a tan solid. The crude intermediate was recrystallized from ethyl acetate/iso-octane to provide 39 g (82%) of 2-methoxycarbonyl-3-(4'-fluorophenyl)-4-(4'-methylthiophenyl)-thienyl-5-carboxylic acid as a white crystalline solid.

Step 3: Preparation of 3-(4'-methylthiophenyl)-4-(4'-fluorophenyl)-thienyl-2,5-dicarboxylic acid To a solution of 2-methoxycarbonyl-3-(4'-fluorophenyl)-4-(4'-methylthiophenyl)-thienyl-5-carboxylic acid (39 g, 93.6 mmol) from Step 2 in 450 ml THF was added 1N NaOH (468 ml). Enough methanol was added to bring reagents back into solution (~75 ml). The reaction was then heated to reflux for 1.5 hours at which time the reaction was determined to be complete by HPLC monitoring. The reaction mixture was washed with diethyl ether (500 ml), acidified with conc. HCl, saturated with NaCl, and extracted twice with 500 ml ethyl acetate. The ethyl acetate was dried over $MgSO_4$ and concentrated in vacuo to yield 36.84 g of 3-(4'-methylthiophenyl)-4-(4'-fluorophenyl)-thienyl-2,5-dicarboxylic acid.

Step 4: Preparation of 3(4'-methylthiophenyl)-4-(4'-fluorophenyl)thiophene

The diacid from Step 3 (36.84 g, 94.9 mmol) was suspended in 400 ml of freshly distilled quinoline and heated to 180–200° C. in an oil bath at which time copper powder (2.6 g) was added in one portion. The reaction was stirred at 180–200° C. for 3 hours, cooled to 130° C., filtered through a medium frit glass funnel then cooled to room temperature. The quinoline was acidified with 3M HCl and extracted twice with diethyl ether (400 ml). The diethyl ether was dried and concentrated to provide 27.83 g of a dark brown solid. The brown solid was dissolved in a minimum amount of ethyl acetate and passed over silica in hexane. The silica was washed with 50% ethyl acetate in hexane until no further product eluted. The product containing fractions were combined and concentrated to provide 25.37 g (89%) of 3-(4'-methylthiophenyl)-4-(4'-fluorophenyl)-thiophene as a white solid.

Step 5: Preparation of 3-(4-methylsulfonylphenyl)-4-(4-fluorophenyl) thiophene 3-(4'-methylthiophenyl)-4-(4'-fluorophenyl)thiophene (21.3 g, 70.9 mmol) from Step 4 was dissolved in 500 ml dichloromethane and cooled to −78° C. To this solution was added 50–60% 3-chloroperoxybenzoic acid (MCPBA) (44.5 g, 142 mmol). The reaction was stirred at −78° C. for 1.5 hours at which time the cooling bath was replaced with an ice bath and the reaction stirred at 0° C. until reaction was complete by monitoring with HPLC. The reaction was warmed to room temperature, washed with 1M $NaHSO_3$ solution (500 ml), saturated $NaHCO_3$ (500 ml) and brine. The reaction solution was dried over $Na_2SO_4$ and concentrated in vacuo. This material was dissolved in 250 ml dichloromethane and 350 ml absolute ethanol was added. The dichloromethane was removed by boiling and the solution cooled to 10° C. for a few hours. 3-(4-Methylfulfonylphenyl)-4-(4-fluorophenyl)-thiophene (16 g) was collected by filtraton on a medium frit funnel. Melting point 190.5–191.5° C.

EXAMPLE 2

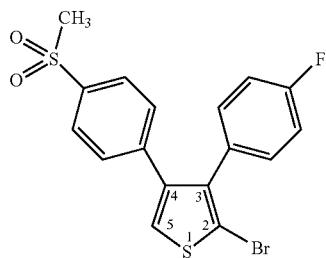

4-(4-Methylsulfonylphenyl)-3-(4-fluorophenyl)-2-bromothiophene

EXAMPLE 3

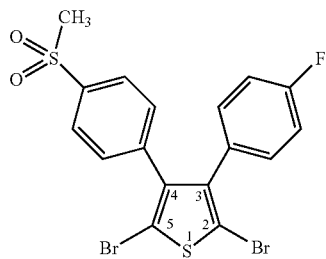

4-(4-Methylsulfonylphenyl)-3-(4-fluorophenyl)-2,5-dibromothiophene 3-(4-Methylsulfonylphenyl)-4-(4-fluorophenyl)-thiophene (102 mg) was dissolved in acetic acid (75 ml) and heated to 90° C. Bromine in acetic acid (0.1 M, 3.07 ml) was added in one portion. The reaction was stirred for 15 minutes at which time the solvent was removed at reduced pressure. The residue was dissolved in a minimum of ethyl acetate and chromatographed on silica, eluting with 2.5% isopropanol in hexane yielding 4-(4-methylsulfonylphenyl)-3-(4-fluorophenyl)-2.5-dibromothiophene (CI MS (M+H): 489/491/493) and 4-(4-methylsulfonylphenyl)-3-(4-fluorophenyl)-2-bromothiophene (CI MS (M+H): 411/413).

EXAMPLE 4

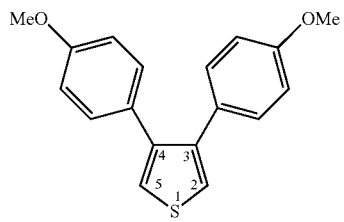

3,4-Bis (4-methoxyphenyl)thiophene

Step 1: Preparation of 2-methoxycarbonyl-3,4-bis-(4-methoxyphenyl)-thienyl-5-carboxylic acid To a stirred solution of 4,4'-bis(methoxy)benzil (3.03 g, 20 mmol) in THF (20 ml), 25% NaOMe in methanol solution (7.4 ml, 32.4 mmol) was added at ambient temperature. This solution was immediately warmed to 65° C. and stirred for 2.5 hours. The reaction was cooled to room temperature and poured into 2M NH₄OH (100 ml) and 100 ml diethyl ether, shaken and separated. The aqueous layer was acidified with concentrated HCl, saturated with NaCl and extracted with ethyl acetate (100 ml). The ethyl acetate was dried over Na₂SO₄ and concentrated in vacuo to provide 1.72 g (40%) of 2-methoxycarbonyl-3,4-bis-(4'-methoxyphenyl)-thienyl-5-carboxylic acid as a white solid. CI MS (M+H): 399.

Step 2: Preparation of 3,4-bis-(4-methoxyphenyl)-thienyl-2,5-dicarboxylic acid

To a solution of 3-methoxycarbonyl-3,4-bis-(4'-methoxyphenyl)-thienyl-5-carboxylic acid (1.6 g, 4.0 mmol) in THF (100 ml) was added 1N NaOH (8.4 ml). Enough methanol was added to bring reagents back into solution (~10 ml). The reaction was heated to reflux for 6 hours at which time the reaction was complete by HPLC monitoring. The THF and methanol were removed at reduced pressure and the residue dissolved in water (300 ml) and diethyl ether (300 ml). The aqueous layer was acidified with conc. HCl, saturated with NaCl and extracted twice with 300 ml ethyl acetate. The ethyl acetate layers were dried over MgSO₄ and concentrated in vacuo to yield 1.45 g (94%) of 3,4-bis-(4-methoxyphenyl)-thienyl-2,5-dicarboxylic acid. CI MS (M+H): 385.

Step 3: Preparation of 3,4-bis (4-methoxyphenyl) thiophene 3,4-bis-(4-methoxyphenyl)-thienyl-2,5-dicarboxylic acid (1.3 g, 3.4 mmol) was suspended in 50 ml of freshly distilled quinoline and heated to 180–200° C. in an oil bath at which time copper powder (0.2 g) was added in one portion. The reaction was stirred at 180–200° C. for 3 hours, cooled to 130° C., filtered through a medium frit glass funnel and cooled to room temperature. The quinoline was acidified with 3N HCl and extracted twice with diethyl ether (40 ml). The diethyl ether layer was dried and concentrated to provide a dark brown solid. The brown solid was dissolved in a minimum amount of ethyl acetate and passed over silica, eluting with hexane. After removal of the hexane, the product was crystallized from hot absolute ethanol to yield 0.9 g (90%) of 3,4-bis (4-methoxyphenyl)thiophene as a white solid. EI MS (M+H): 296.

EXAMPLE 5

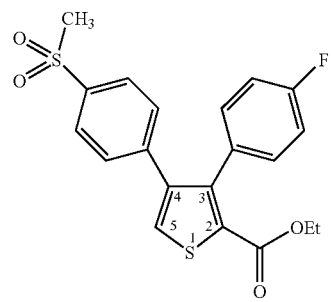

Ethyl [4-(4-methylsulfonylphenyl)-3-(4-fluorophenyl)thien-2-yl]carboxylate

Step 1: Preparation of 2-ethoxycarbonyl-3-(4-fluorophenyl)-4-(4-methylthiophenyl)thiophene A mixture of 2-ethoxycarbonyl-3-(4-fluorophenyl)-4-(4-methylthiophenyl)-thienyl-5-carboxylic acid and 2-caroethoxy-3-(4-methylthiophenyl)-4-(4-fluorophenyl)-thienyl-5-carboxylic acid (714 mg), described in Example 1, was suspended in 75 ml of freshly distilled quinoline and heated to 180–200° C. in an oil bath at which time copper powder (0.2 g) was added in one portion. The reaction was stirred at 180–200° C. for 3 hours, cooled to 130° C., filtered through a medium frit glass funnel and cooled to room temperature. The quinoline was acidified with 3N HCl and extracted twice with diethyl ether (40 ml). The diethyl ether was dried and concentrated to provide a dark brown solid. The brown solid was dissolved in a minimum amount of ethyl acetate and passed over silica, eluting with hexane followed by 5% ethyl acetate in hexane to the yield 2-ethoxycarbonyl-3-(4-fluorophenyl)-4-(4-methylthiophenyl)thiophene; CI MS (M+H): 373.

Step 2: Preparation of 2-ethoxycarbonyl-3-(4-fluorophenyl)-4-(4-methylsulphonylphenyl)thiophene 2-ethoxycarbonyl-3-(4-fluorophenyl)-4-(4-methylthiophenyl)thiophene from Step 1 (93.1 mg, 0.25 mmol) was dissolved in 10 ml dichloromethane and cooled to −78° C. To this solution was added 50–60% MCPBA (173 mg, 0.5 mmol). The reaction was stirred at −78° C. for 1.5 hours at which time the cooling bath was replaced with an ice bath and the reaction stirred at 0° C. until the reaction was complete as monitored by HPLC. The reaction was warmed to room temperature and washed with 1M NaHSO$_3$ solution (10 ml), saturated NaHCO$_3$ (10 ml) and brine. The solution was dried over Na$_2$SO$_4$ and concentrated in vacuo. This residue was dissolved in ethyl acetate and chromatographed on silica, eluting with a gradient from 1%–4% isopropanol in hexane yielding 2-ethoxycarbonyl-3-(4-fluorophenyl)-4-(4-methylsulphonylphenyl)thiophene as a white solid. $^1$H NMR(CDCl$_3$) δ1.2p (t, 3h, J=7.0 Hz), 3.0 (s, 3h), 4.22 (q, 2h, J=7.0 Hz), 7.0 (m, 2 h), 7.11 (m, 2h), 7.23 (d, 2h, J=8.4 Hz), 7.6 (s, 1H), 7.8 (d, 2h, J=8.4 Hz).

EXAMPLE 6

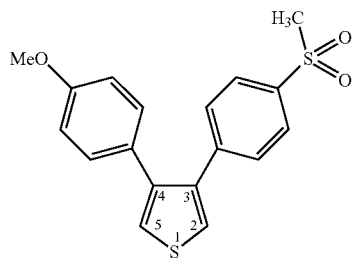

3-(4-Methylsulfonylphenyl)-4-(4-methoxyphenyl)thiophene

Step 1: Preparation of 3-thioacetyl-4'-methoxy acetophenone

Potassium thioacetate (2.28 g, 20 mmol) was added to a solution of 2-bromo-4'-methoxy acetophenone (4.58 g, 20 mmol) in absolute ethanol (150 ml). The reaction was stirred at ambient temperature under nitrogen for 16 hours at which time the white precipitate that had formed was filtered and the ethanol removed at reduced pressure. The residue was dissolved in dichloromethane (250 ml) and washed with water (200 ml), brine (200 ml), dried over Na$_2$SO$_4$ and the solvent removed at reduced pressure. The resulting residue was chromatographed on silica with a gradient from 10%–35% ethyl acetate in hexane to yield 3.4 g (76%) of 2-thioacetyl-4'-methoxy acetophenone. $^1$H NMR (CDCl$_3$) δ2.36 p (s, 3h), 3.84 (s, 3h), 4.33 (s, 2h), 6.9 (d, 2h, J=9.2 Hz), 7.9 (d, 2h, J=9.2 Hz).

Step 2: Preparation of Diketone

2-Thioacetyl-4'-methoxy acetophenone (449 mg, 2 mmol) and 2-chloro-4'-methylthioacetophenone (401 mg, 2 mmol) was dissolved in ethanol (20 ml). To this solution was added NH$_4$OH (20 M, 1 ml) and the reaction was stirred for 16 hours at ambient temperature. The ethanol was removed at reduced pressure, the residue was dissolved in ethyl acetate (50 ml) and washed with 1N HCl (30 ml) and brine (30 ml). The ethyl acetate was dried over Na$_2$SO$_4$ and the solvent was removed at reduced pressure. The residue was chromatographed on silica eluting with 20% ethyl acetate in hexane to yield the diketone (290 mg, 42%). CI MS (M+H): 347.

Step 3: Preparation of Diol

The diketone from Step 2 (173 mg) was dissolved in anhydrous THF (10 ml) and cooled to −7° C. To this solution was added TiCl4 (255.1 μl, 2.3 mmol) and zinc powder (300 mg). The reaction was stirred at ambient temperature for 3 huors at which time 10% aq K$_2$CO$_3$ (20 ml) and dichloromethane (20 ml) were added and the entire reaction poured through celite. The aqueous and organic layers were separated. The organics were washed with water (20 ml), dried over Na$_2$SO$_4$ and the solvent removed at reduced pressure. The residue was chromatographed on silica, eluting with a gradient from 10%–30% ethyl acetate in hexane to yield 75 mg (31%) of diol. CI MS (M+H): 349.

Step 4: Preparation of 3-(4-methylthiophenyl)-4-(4-methoxyphenyl)thiophene

Diol from Step 3 (65 mg) and p-toluenesulphonic acid (15 mg) were dissolved in toluene (10 ml) and heated to reflux under nitrogen for 1 hour. The solution was cooled and filtered and diethyl ether (50 ml) added. The organics were washed twice with saturated NaHCO$_3$ (2×50 ml), once with brine (50 ml), dried over Na$_2$SO$_4$ and the solvent removed at reduced pressure. The residual oil was dissolved in a minimum amount of ethyl acetate and chromatogrlaphed on silica, eluting with 2% ethyl acetate in hexane to yield 3-(4-methylthiophenyl)-4-(4-methoxyphenyl)thiophene (53 mg, 95%), EI MS (M+H): 312.

Step 5: Preparation of 3-(4-methylsulphonylphenyl)-4-(4-methoxyphenyl)thiophene 3-(4-Methylthiophenyl)-4-(4-methoxyphenyl)thiophene from Step 4 (36.5 mg, 0.12 mmol) was dissolved in dichloromethane (10 ml). To this solution was added 3-chloroperoxybenzoic acid (MCPBA) (88.7 mg of 50% MCPBA) and the reaction stirred under nitrogen for 6 hours. Once the reaction was complete, dichloromethane (25 ml) was added and the reaction washed with Na$_2$S$_2$O$_5$ in water (1 g in 25 ml), saturated NaHCO$_3$ (2×25 ml), brine (25 ml), dried over Na$_2$SO$_4$ and the solvent removed at reduced pressure. The crude solid was purified by crystallization from dichloromethane and isoctane to yield 3-(4-methylsulphonylphenyl)-4-(4-methoxyphenyl)thiophene (40 mg, 98%). CI MS (M+H): 344.

EXAMPLE 7

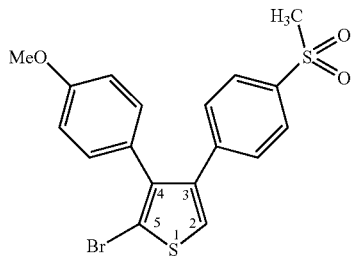

3-(4-Methylsulfonylphenyl)-4-(4-methoxyphenyl)-5-bromothiophene 3-(4-methylsulphonylphenyl)-4-(4-methoxyphenyl) thiophene from Example 6 (9.3 mg) was dissolved in acetic acid (10 ml) and heated to 90° C. at which time Br$_2$ in acetic acid (1.0 M, 27 µl) was added in one portion. The reaction was stirred for 15 minutes at which time the solvent was removed at reduced pressure. The residue was dissolved in a minimum of ethyl acetate and chromatographed on silica, eluting with 2.5% isopropanol in hexane, yielding 3-(4-methylsulfonylphenyl)-4-(4-methoxyphenyl)-5-bromothiophene. CI MS (M+H): 423/425.

EXAMPLE 8

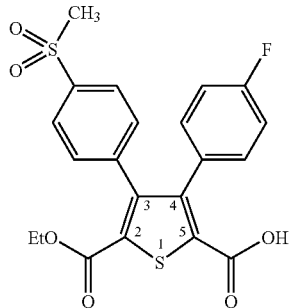

2-Ethoxycarbonyl-4-(4-fluorophenyl)-3-(4-methanesulfonylphenyl)-thienyl-5-carboxylic Acid Step 1: Preparation of 1-(4'-thiomethylphenyl)-1-(trimethylsiloxy) acetonitrile A 1L 3-necked round-bottomed flask equipped with magnetic stirrer, nitrogen inlet, reflux condenser, constant pressure addition funnel and thermometer was charged with 4'-methylthiobenzaldehyde (33.5 ml, 0.252 mol) and 300 ml of dichloromethane. The addition funnel was charged with trimethylsilylcyanide (25.0 g, 0.252 mol) dissolved in 100 ml dichloromethane. The stirrer was started and approximately 10 ml of the trimethylsilyl cyanide solution was added from the addition funnel. As no exotherm was noted, zinc iodide (0.50 g, 0.0016 mol) was added to the reaction. An exotherm of approximately 3° C. was noted, and the addition of the trimethylsilylcyanide solution was continued over about 0.75 hour. During the addition, the exotherm produced warmed the reaction to reflux. The reaction was stirred for one hour, during which time it cooled to room temperature, and the mixture was poured into a separatory funnel charged with water (300 ml). The layers were separated, and the water layer was extracted once with dichloromethane (200 ml). The combined organic layers were washed with brine (200 ml), dried over anhydrous MgSO4, filtered, and concentrated in vacuo to yield a light orange oil (61.05 G, 96%), which crystallized upon standing, of 1-(4'-thiomethylphenyl)-1-(trimethylsiloxy) acetonitrile, $^1$H NMR (CDCl$_3$/300 MHz) δ7.42(m, 4H), 5.49(s, 1H), 2.53 (s, 3H), 0.26 (s, 9H).

Step 2: Preparation of 2-(4-thiomethylphenyl)-2-hydroxy-4'-fluoroacetophenone

An oven-dried, 1L four-necked round-bottomed flask equipped with mechanical stirrer, reflux condenser, nitrogen inlet, constant pressure addition funnel and thermometer was charged with magnesium turnings (3.31 g, 0.136 mol) and anhydrous THF (200 ml). The addition funnel was charged with 4-bromo-1-fluorobenzene (15.1 ml, 0.136 mol) dissolved in anhydrous THF (100 ml). Approximately 5 ml of the 4-bromo-1-fluorobenzene solution was added to the reaction flask, and an immediate exotherm of 2° C. was observed. The remaining 4-bromo-1-fluorobenzene solution was added over ca. 0.75 hour. During the addition, the exotherm produced warmed the reaction to reflux. Upon complete addition, the reaction was stirred without temperature control for ca. 0.75 hour then cooled to 11° C. The addition funnel was charged with 1-(4-thiomethylphenyl)-1-(trimethylsiloxy)-acetophenone (61.05 G, 0.242 mol) dissolved in anhydrous tetrahydrofuran (200 ml). This solution was added over ca. 0.5 hour, while the reaction temperature was maintained lower than 18° C. During the addition, a thick brown oil precipitated, but was kept in suspension by mechanical stirring. The reaction was stirred without temperature control for one hour and quenched by addition of 3 N HCl (300 ml). After stirring for one hour, the solution was transferred to a separatory funnel and extracted with ethyl acetate (2×300 ml). The combined organic solution was dried over anhydrous MgSO4, filtered, and concentrated in vacuo to yield a dark oil. The oil was dissolved in a minimum amount of boiling ethyl acetate, and isooctane was added until the solution turned cloudy. Upon cooling, tan crystals separated. The suspension was cooled to 0° C., held for 0.5 hour, filtered and washed with hexane to provide, after air-drying, 2-(4-thiomethylphenyl)-2-hydroxy-4'-fluoroacetophenone (16.6 g, 53%). $^1$H NMR (CDCl$_3$/300 MHz) δ7.93(m, 2H), 7.20(m, 4H), 7.06(m, 2H), 5.86(s, 1H), 2.43(s, 3H); $^{19}$F NMR (CDCl$_3$/282.2 MHz) −103.036(t, J=6.77 Hz).

Step 3: Preparation of 4-fluoro-4'-thiomethylbenzil

A 500 ml three-necked round-bottomed flask equipped with reflux condenser, thermometer and provisions for magnetic stirring was charged with 2-(4-thiomethylphenyl)-2-hydroxy-4'-fluoroacetophenone from Step 2 (15.0 g, 54.48 mmol) and 300 ml of glacial acetic acid. The solution was warmed to ca. 90° C., when Bi$_2$O$_3$ (10.16 g, 21.79 mmol) was added. The suspension was stirred at reflux for 16 hours, cooled to room temperature. The insoluble inorganics were filtered onto a pad of Celite and washed with glacial acetic acid (50 ml). Water (700 ml) was added, and the resulting suspension was cooled to ca. 15° C., held for 0.5 hour, filtered, washed with water and dried to yield 4-fluoro-4'-thiomethylbenzil (11.98 g, 80%) as a dark yellow solid. $^1$H NMR (CDCl$_3$/300 MHz) δ8.01 (m, 2H), 7.86(m, 2H), 7.29(m, 2H), 7.18(m, 2H), 2.53(s, 3H); $^{19}$F NMR (CDCl$_3$/282.2 MHz −101.58(m).

Step 4: Preparation of 4-fluoro-4'-methanesulfonylbenzil

A 500 ml one-neck round-bottom flask equipped for magnetic stirring was charged with 4-fluoro-4'- thiomethylbenzil from Step 3 (10.0 g, 36.46 mmol) and dichloromethane (200 ml) and cooled to 0° C. m-Chloroperbenzoic acid (26.42 G, 50 W %, 153.1 mmol) was added, and the suspension was stirred without temperature control for 16 hours. The reaction was poured into aqueous Na$_2$S$_2$O$_5$ (5%, 200 ml), and the dichloromethane was evaporated in vacuo. The residue was dissolved in ethyl acetate (200 ml) and washed with 5% Na$_2$S$_2$O$_5$ (2×200 ml) and saturated NaHCO$_3$ (2×200 ml), dried over anhydrous MgSO$_4$, filtered and the solvent evaporated in vacuo to yield 4-fluoro-4'-methylsulfonylbenzil (10.8 g, 96%) as a white solid. $^1$H NMR (CDCl$_3$/300 MHz) δ8.10 (m, 6H), 7.21(m, 2H), 3.08(s, 3H); $^{19}$F NMR (CDCl$_3$/282.2 MHz −100.21(m).

Step 5: Preparation of 5-ethoxycarbonyl-4-(4-fluorophenyl)-3-(4-methanesulfonylphenyl)-thienyl-2-carboxylic acid and 2-ethoxycarbonyl-4-(4-fluorophenyl)-3-(4-methanesulfonylphenyl)-thienyl-5-carboxylic acid A 500 ml three-neck round-bottom flask equipped with a reflux condenser, thermometer and provisions for magnetic stirring was charged with 4-fluoro-4'-methanesulfonylbenzil from Step 4 (2.5 g, 8.16 mmol) and diethyl thiodiglyoolate (3.03 g, 14.69 mmol) dissolved in tetrahydrofuran (200 ml). Sodium ethoxide in ethanol (9.4 ml; 21 W %, 22.9 mmol) was added, and the reaction was warmed to reflux. After 1.5 hour, the reaction was cooled to room temperature and acidified with 1N HCl (100 ml). The organic solvents were evaporated in vacuo, and the aqueous residue was extracted with diethyl ether (2×200 ml). The combined organic soluton was washed with 10% NH$_4$OH solution (3×100 ml). The combined basic aqueous solution was then acidified with conc. HCl to pH 2. The resulting suspension of oil in water was extracted with dichloromethane (3×100 ml). The combined organic solution was dried over anhydrous magnesium sulfate, filtered and concentrated in vacuo to an oil. Crystallization from hot ethanol/water yielded, upon drying, yielded 5-ethoxycarbonyl-4-(4-fluorophenyl)-3-(4-methanesulfonylphenyl)-thienyl-2-carboxylic acid and 2-ethoxycarbonyl-4-(4-fluorophenyl)-3-(4-methanesulfonylphenyl)-thienyl-5-carboxylic acid as a 50:50 mix of ester regioisomers (2.38 g, 65%), as a light tan solid $^1$H NMR (CDCl$_3$/300 MHz) δ 7.78(m, 2H), 7.21(m, 2H), 6.93(m, 4H) 4.23(m, 2H) 3.05(s, 3H), 1.22(m, 3H); $^{19}$F NMR (CDCl$_3$/282.2 MHz) −112.93 (m) −113.22 (m). Mass spectrum (M+H): 449.

EXAMPLE 9

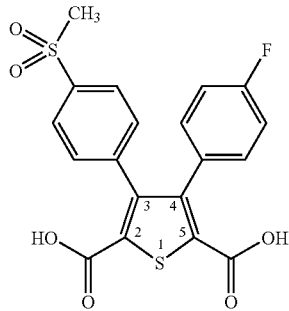

4-(4-Fluorophenyl)-3-(4-methanesulfonylphenyl)-thienyl-2,5-dicarboxylic Acid

The acidic mother liquor of Example 8, step 5, was concentrated in vacuo to approximately one-third of its original volume (180 ml). The resulting suspension was cooled to 0° C., held for thirty minutes, filtered and washed with 1 N HCl to yield, upon drying, 4-(4-fluorophenyl)-3-(4-methanesulfonylphenyl)thiophene-2,5-dicarboxylic acid (0.60 g; 17.5%) as a white solid. $^1$H NMR (CDCl$_3$/300 MHz) δ8.13(m, 2H) 8.04(m, 2H) 7.64(m, 2H), 7.47 (m, 2H).

EXAMPLE 10

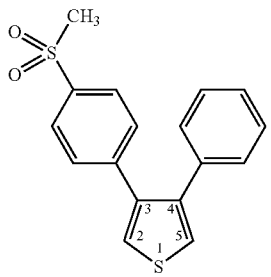

3-(4-Methanesulfonylphenyl)-4-phenyl-thiophene

A 100 mL one-neck round-bottom flask, equipped with provisions for magnetic stirring, was charged with aqueous ethanol (5 mL) and 3-(thiomethylphenyl)-4-phenyl-thiophene (9 mg, 0.032 mmol), prepared according to procedures similar to that exemplified in Example 1, with the substitution of the appropriate substituted benzil (4'-thiomethylbenzil) in Step 3. Oxone (59 mg, 0.096 mmol) was added, and the suspension was stirred at room temperature for 16 hours. Water (75 mL) was added, and the product precipitated. The suspension was cooled to 0° C. and held for one hour. The product was filtered, washed with water (5 mL), and dried to yield 3-(methanesulfonylphenyl)-4-phenyl-thiophene (4.1 mg, 41%) as a white solid. $^1$H NMR (CDCl$_3$/300 MHz) δ 7.81(m, 2H), 7.43–7.27(m, 7H), 7.16 (m, 2H), 3.06(s, 3H). Mass spectrum (M+H): 314.

EXAMPLE 11

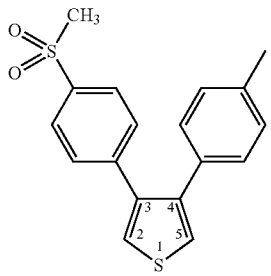

3-(4-Methanesulfonylphenyl)-4-(4-methylphenyl)-thiophene 3-(4-Methanesulfonylphenyl)-4-(4-methylphenyl)thiophene was prepared in a manner similar to that exemplified in Example 10, with the substitution of the appropriate substituted benzil (4'-thiomethyl-4-methylbenzil) from Step 3. $^1$H NMR (CDCl$_3$/300 MHz) δ7.81(m, 2H), 7.41–7.31(m, 4H), 7.06(m, 4H), 3.06(s, 3H), 2.35(s, 3H). Mass spectrum (M+H): 329.

EXAMPLE 12

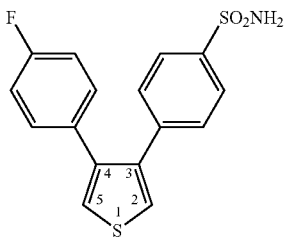

4-[4-(4-Fluorophenyl)thien-3-yl]
benzenesulfonamide

To a solution of 3-(4-methylsulfonylphenyl)-4-(4-fluorophenyl)thiophene (0.332 g, 1.0 mmol) in THF (8 mL) at −70° C. under nitrogen was added 1.6 M n-butyl lithium in hexane (0.66 mL, 1.05 mmol) slowly, via syringe, and the mixture stirred at −70° C. for 20 minutes and then at room temperature (25° C.) for 1 hour. After cooling to −70° C., a 1.0 M solution of tri-n-butyl borane in THF (1.15 mL, 1.15 mmol) was added and the mixture allowed to warm slowly to 0° C. for 1 hour, warmed to room temperature for 2 hours, and finally stirred at reflux overnight (18 hours). After cooling to room temperature and stirring for 3 hours, water (0.8 mL) was added followed by sodium acetate (0.6 g) and hydroxylamino-O-sulfonic acid (0.41 g). After stirring at room temperature overnight, the mixture was poured into 3 volumes of ethyl acetate, and the organic layer washed with water and brine and dried over MgSO$_4$. After solvent removal, the white solids (a mixture of product and starting material) were separated via flash chromatography on silica gel using a 15% ethyl acetate/85% toluene eluant to yield the benzenesulfonamide as a white solid (59 mg, mp 194–195° C.). Anal. Calc'd for $C_{16}H_{12}NO_2S_2F$: C, 57.64; H, 3.63; N, 4.20. Found: C, 57.37; H, 3.69; N, 3.99.

EXAMPLE 13

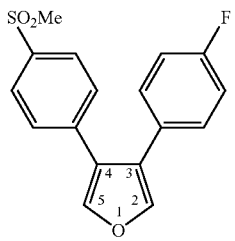

3(4-Fluorophenyl)-4-(methylsulfonylphenyl)furan

Step 1: Preparation of 4-(methylthio) acetophenone

To a stirred solution of 4-(methylthio)benzonitrile (50 g, 340 mmol) in THF (2L) at −78° C., was added methyllithium (282 ml, 1.4 M in diethyl ether, 390 mmol) over a period of ten minutes. The solution was stirred at −78° C. for one hour and then the dry ice bath was removed. After five hours, 100 ml of water followed by 200 ml of 3N HCl were added to the reaction mixture and it was stirred overnight. Concentration in vacuo gave a residue which was partitioned between ethyl acetate and water. The water layer was extracted with three portions of ethyl acetate and the combined ethyl acetate layers were dried (MgSO$_4$). Concentration in vacuo gave 58 g of crude 4-(methylthio) acetophenone as a yellow solid: $^1$H NMR (CDCl$_3$) δ2.52 (s, 3H), 2.57 (s, 3H), 7.26 (d, J=8.7 Hz, 2H), 7.87 (d, J=8.7 Hz, 2H). The sample was used without further purification.

Step 2: Preparation of 4-(methylsulfonyl) acetophenone

To a solution of the acetophenone prepared in Step 1 (11.73 g, 71.1 mmol) in dichloromethane (500 ml) at ambient temperature was added m-chloroperoxybenzoic acid (50%, 61.14 g, 177 mmol) in portions over 20 minutes. The reaction was stirred for two hurs, quenched slowly with sodium meta-bisulfite, washed with three 100 ml portions of saturated sodium bicarbonate, dried (MgSO$_4$), and concentrated in vacuo to give 11.91 g (91%) of 4-(methylsulfonyl) acetophenone as an off-white solid: $^1$H NMR (CDCl$_3$) δ2.67 (s, 3H), 3.08 (s, 3H), 8.06 (d, J=9 Hz, 2H), 8.14 (d, J=9 Hz, 2H).

Step 3: Preparation of 2-bromo-4'-(methylsulfonyl) acetophenone

To a stirred solution of the acetophenone prepared in Step 2 (11.91 g, 60.5 mmol) in glacial acetic acid (133 ml) and hydrochloric acid (0.11 ml) at ambient temperature, was added a soluton of bromine (8.22 g, 51.4 mmol) in glacial acetic acid (9.3 ml) over a period of three hours. The reaction mixture was diluted with water (500 ml) and extracted with chloroform. The combined chloroform extracts were dried (MgSO$_4$) and concentrated in vacuo to give 15.66 g of crude 2-bromo-4'-(methylsulfonyl)acetophenone: $^1$H NMR (CDCl$_3$) δ3.10 (s, 3H), 4.45 (s, 2H), 8.08 (d, J=9 Hz, 2H), 8.17 (d, J=9 Hz, 2H). The sample was used without further purification.

Step 4: Preparation of 2-(4'-methylsulfonylphenacyl)-4-fluorophenyl acetate

The bromo acetophenone prepared in Step 3 (8.9 g, 28.9 mmol) was added to a stirred solution of 4-fluorophenyl acetic acid (4.45 g, 28.9 mmol) in triethylamine (3.26 g, 31.8 mmol) and acetonitrile (275 ml) at ambient temperature and stirred for 30 minutes. The reaction was concentrated in vacuo and the residue partitioned between ethyl acetate and water. The organic fraction was dried (MgSO$_4$) and concentrated in vacuo. The residue was purified by silica gel chromatography (40% ethyl acetate/hexane) to give 6.87 g (68% yield) of 2-(4'-methylsulfonylphenacyl)-4-fluorophenyl acetate as a colorless solid: $^1$H NMR (CDCl$_3$) δ3.08 (s, 3H), 3.79 (s, 2H), 5.35 (s, 2H), 7.06 (s, t, J=9 Hz, 2H), 7.32 (q, J=6, 9 Hz, 2H), 8.06 (s, 4H).

Step 5: Preparation of 3-(4-fluorophenyl)-4-(4-methylsulfonylphenyl)-2(5H)-furanone The phenylacetate prepared in Step 4 (4.10 g, 11.7 mmol) was combined with triethylamine (6.52 ml, 46.8 mmol), p-toluenesulfonic acid (4.89 g, 25.7 mmol), and 4 Å molecular sieves (12.0 g) in acetonitrile (117 ml) and heated to reflux for 16 hours. The reaction was concentrated in vacuo and the residue partitioned between dichloromethane and water. The dichloromethane fraction was dried (MgSO$_4$) and concentrated in vacuo. Recrystallization from hexane/ethyl acetate (2:1) gave 3.65 g (94%) of 3-(4-fluorophenyl)-4-(4-methylsulfonylphenyl)-2(5H)-furanone as a solid: mp 166–167° C.; $^1$H NMR (CDCl$_3$) δ 3.08 (s, 3H), 5.19 (s, 2H), 7.10 (t, J=9 Hz, 2H), 7.42 (q, J=6, 9 Hz, 2H), 7.52 (d, J=9 Hz, 2H), 7.97 (d, J=9 Hz, 2H); HRMS. Calc'd for M+H: 333.0519. Found 332.0501. Anal. Calc's for $C_{17}H_{13}FO_4S$: C, 61.44; H, 3.94; O, 19.26. Found: C, 61.11; H, 4.06; O, 19.32.

Step 6: Preparation of 3-(4-fluorophenyl)-4-(4-methylsulfonylphenyl)furan

Under nitrogen, borane dimethyl sulfide complex (2M in toluene, 3.6 ml, 7.2 mmoles) was added with stirring to the furanone prepared in Step 5 (0.6 g, 1.8 mmoles) in 10 ml of THF. After two hours, additional borane dimethyl sulfide complex (2M in toluene, 5.4 ml, 10.8 mmoles) was added. The reaction was stirred at ambient temperature for one hour and at 5° C. for 62 hours. The reaction was concentrated in vacuo and the residue slowly mixed with 50 ml of ice water and extracted with three 25 ml portions of ethyl acetate. The combined organic fractions were washed with 25 ml brine, dried (MgSO$_4$), and concentrated in vacuo. Purification by silica gel chromatography (5% ethyl acetate/dichloromethane) gave 0.22 g (38%) of a colorless solid. Recrystallization from ethyl acetate/hexane gave 3-(4-fluorophenyl)-4-(4-methylsulfonylphenyl)furan: mp 160–161° C.; $^1$H NMR (CDCl$_3$) δ3.07 (s, 3H), 6.99–7.07 (m, 2H), 7.13–7.21 (m, 2H), 7.37–7.42 (m, 3H), 7.56 (d, J=1.8 Kz, 1H), 7.66 (d J=1.6 Hz, 1H), 7.83–7.89 (m, 2H); $^{19}$F NMR (CDCl$_3$) δ–114.80 to –114.90 (m); MS m/e (M+H) 317(73), (M+) 316(100); HRMS. Calc'd for M+H: 316.0569. Found: 316.0571. Anal. Calc'd for C$_{17}$H$_{13}$FO$_3$S: C, 64.55; H, 4.14; F, 6.01; S, 10;0.13. Found: C, 64.59; H, 4.02; F, 6.22; S, 10.52.

EXAMPLE 14

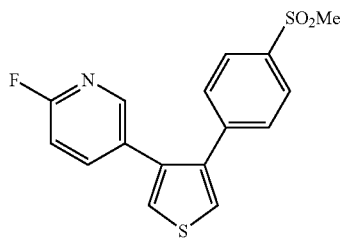

3-(4-Methylsulfonylphenyl)-4-(4-fluoropyridin-3-yl) thiophene

Step 1: Preparation of 4-(4-methylthiophenyl)-3-bromothiophene

4-Bromothioanisole (4.197 g, 20.7 mmol.) was dissolved in 50 ml of dry THF and cooled to –78° C. N-butyllithium (2.5M, 9.1 ml, 22.77 mmol) was added via syringe and allowed to stir for 30 minutes. 1.0 M Zinc bromide in THF (24.0 ml) was added and the reaction warmed to room temperature. A solution of the dibromothiophene (1 eq., 20.7 mmol, 5.0 g), 25 ml of THF, and tetrakis (triphenylphosphine) palladium(0) (5%, 1 mmol.) was added via syring to the zinc-thioanisole solution. The reaction was stirred at reflux overnight. The reaction mixture was concentrated, dissolved in ethyl acetate, washed with sat. ammonium chloride, followed by sat. brine, dried (MgSO$_4$), and reconcentrated to give 2.0 g of crude material. Purification by silica gel chromatography (Waters LC 2000) with hexane gave 1.0 g (20%) of pure monosubstituted thiophene material. NMR(CDCl$_3$): δ 2.52(s, 3H), 7.22(d, J=6Hz, 1H), 7.30(d, J=8 Hz, 2H).

Step 2: Preparation of 4-)4-methylthiophenyl)-3-(4-fluorophenyl)thiophene

The monosubstituted thiophene (1.0 g, 3.5 mmol) from Step 1 was dissolved in 15 ml of tetrahydrofuran and cooled to –78° C. prior to addition of n-butyllithium (2.5 M, 1.1 eq, 3.9 mmol., 1.5 ml). The reaction was stirred for 30 minutes at –78° C., zinc bromide in tetrahydrofuran (1.0 M, 1.2 eq, 4.2 mmol.) was added, and the solution was allowed to warm to 23° C. A mixture of 2-fluoro-5-bromo-pyridine (3 eq, 10.5 mmol, 1.85 g), nickel (+2) (diphenylpalladium) chloride (0.5 eq, 100 mg) and tetrahydrofuran (20 ml) was added and the reaction and was stirred at reflux overnight. The solution was concentrated in vacuo. The residue was dissolved in ethyl acetate and washed with water, dried (MgSO$_4$) and reconcentrated. Purification by silica gel chromatography (Waters, LC-2000) with hexane gave 330 mg (33%) of the desired 4-(4 methylthiophenyl)-3-(4-fluorophenyl)thiophene as an oil: NMR (CDCl$_3$): δ2.49(s, 3H), 6.81(dd, J=2 Hz, J=8 Hz, 1H), 7.08(d, J=8 Hz, 2H), 7.16(d, J=8 Hz, 2H), 7.35(dd, J=2 Hz, J=8 Hz, 2H), 7.49(td, J=2 Hz, J=6 Hz, 1H), 8.14(d, J=1 Hz, 1H).

Step 3: Preparation of 4-(4methylsulfonylphenyl)-3-(4-fluorophenyl) thiophene The 4-(4-methylthiophenyl)-3-(4-fluorophenyl) thiophene (330 mg, 1.1 mmol.) FROM STEP 2 was dissolved in 9.0 ml of dichloromethane, to which meta-chloroperbenzoic acid (MCPBA) (2 eq, 2.2 mmol) was added in one portion. The reaction was stirred for 20 minutes at 23° C. and quenched with 500 mg of sodium metabisulfite in 10 ml of water. The organic layer was diluted with dichloromethane and washed repeatedly with sat. sodium bicarbonate and sat. brine. The organic layer was dried (MgSO$_4$) and concentrated in vacuo. Recrystallization from ethyl acetate/hexane (1:3) gave 266 mg (73%) of 4-(4 methylsulfonylphenyl)-3-(4-fluorophenyl)thiophene: mp 190–191° C. (dec)); NMR (CDCl$_3$) δ3.39(s, 3H), 6.84–6.90 (m, 1H), 7.36(d, J=8 Hz, 2H), 7.42(d, J=2 Hz, 1H), 7.45–7.53(m, 2H), 7.88(d, J=7 Hz, 2H), 8.10(bs, 1H).

Anal. Calc'd for C$_{16}$H$_{12}$NFO$_2$S$_2$: C, 57.59; H,3.60; N, 4.20; F, 5.67. Found: C, 57.39; H,3.75; N, 3.97; F 5.50.

EXAMPLE 15

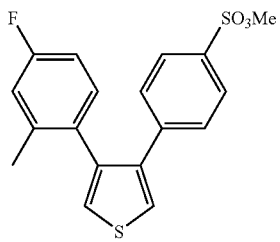

3-(4-Methylsulfonylphenyl)-4-(2-methyl-4-fluorophenyl) thiophene

Step 1: Preparation of 2-methyl-4-fluorophenyl Boronic Acid

2-Bromo-5-fluorotoluene (52.9 mmol, 10 g) in 400 ml of tetrahydrofuran was cooled to –78° C. and n-butyllithium (2.5 M, 58.2 mmol) was added. The solution was stirred for 20 minutes, trimethoxy borane (3 eq, 0.16 mol) was added, and the reaction was allowed to warm to room temperature overnight. Sodium hydroxide (60 ml of 1.25 M) was added and the reaction was stirred for 30 minutes. The tetrahydrofuran was removed in vacuo. The remaining aqueous layer was diluted and extracted with diethyl ether. The aqueous layer was adjusted to pH 3 with 2M HCl and extracted with ethyl acetate, which was dried (MgSO$_4$) and concentrated in vacuo to give 6.57 g (81%) of a colorless solid: MS(FAB) m/e (rel. intensity) 154(48), 136(100).

Step 2: Preparation of 3-(4-methylthiophenyl)-4-(2-methyl-4-fluorophenyl)thiophene The mono-substituted thiophene from Example 14 (1.8 mmol, 520 mg) was combined with the 2-methyl-4-fluorophenyl boronic acid (2 eq, 3.6 mmol, 562 mg) in 8.0 ml of toluene, 4.3 ml of 2 M sodium carbonate, 10 ml of ethanol and tetrakis(triphenylphosphine)-palladium(0) (1.0 g) and was stirred at reflux overnight. The reaction was concentrated in vacuo and the residue was partitioned between toluene and water. The toluene layer was dried (MgSO$_4$) and reconcentrated in vacuo. The residue was purified via silica chromatography (Waters, LC-2000) in 97% hexane/ethyl acetate to give 3-(4-methylthiophenyl)-4-(2-methyl-4-fluorophenyl)thiophene (420 mg) as a semi-solid. NMR (CDCl$_3$) δ1.90(s, 3H), 2.43(s, 3H), 6.8–6.9(m, 2H), 7.05(q, J=8 Hz, 4H), 7.12–7.18(m, 2H), 7.33(d, J=2 Hz, 1H).

Step 3: Preparation of 3-(4-methylsulfonylphenyl)-4-(2-methyl-4-fluorophenyl) thiophene 3-(4-methylthiophenyl)-4-(2-methyl-4-fluorophenyl) thiophene (420 mg, 1.34 mmol) from Step 2 was dissolved in 20 ml of dichloromethane and treated with meta-chloroperbenzoic acid (2 eq, 2.68 mmol). The reaction was stirred at room temperature for 20 minutes, diluted with dichloromethane, quenched with sodium metabisulfite (550 mg in 10 ml water) washed with sat. sodium bicarbonate, dried (MgSO$_4$) and concentrated in vacuo. The residue was crystallized from ethyl acetate/hexane (1:2) to give 3-(4-methylsulfonylphenyl)-4-(2-methyl-4-methylsulfonylphenyl)-4-(2-methyl-4-fluorophenyl) thiophene (200 mg): mp 158–160° C.; NMR (CDCl$_3$): δ1.8(s, 3H), 3.1(s, 3H), 6.82–6.92(m, 2H), 7.12–7.18(m, 1H), 7.22(d, J=2 Hz, 1H), 7.30(d, J=8 Hz, 2H), 7.49(d, J=2 Hz, 1H, 7.77(d, J=8 Hz, 2H); MS(FAB) m/e (rel. intensity) 353(m+Li), (70), 347(40), 220(35). Anal. Calc'd for C$_{18}$H$_{15}$FO$_2$S$_2$: C, 62.45, H, 4.34, F, 5.46. Found: C, 62.14, H, 4.47, F, 5.20.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.,* 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplanter injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Blivan, *Laboratory Models for Testing NSAIDs,* in *Non-steroidal Anti-Inflammatory Drugs,* (J. Lombardino, ed. 1985)). Results are shown in Table I.

Rat Carrageenan-induced Analgesia Test

The analgesia test using rat carrageenan was performed with materials, reagents and procedures essentially as described by Hargreaves, et al., (*Pain,* 32, 77 (1988)). Male Sprague-Dawley rats were trested as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 20 mg/kg body weight |
|---|---|---|
| 1 | | 8 |
| 2 | 30 | 0* |
| 4 | 22 | |
| 14 | 30 | 28 |
| 15 | 20 | |

*@ 3 mpk

Evaluation of COX-I and COX-II Activity in vitro a. Preparation of Recombinant COX Baculoviruses A 2.0 kb fragment containing the coding region of either human or murine COX-I or human or murine COX-II was cloned into a BamH1 site of the baculovirus transfer vector pVL1393 to generate the baculovirus transfer vector. Recombinant baculoviruses were isolated by transfecting 4 μg of baculovirus transfer vector DNA into SF9 cells (2×10e8) along with 200 ng of linearized baculovirus plasmid DNA by the calcium phosphate method. Recombinant viruses were purified by three rounds of plaque purification and high titer (10E7-10E8 pfu/ml) stocks of virus were prepared. For large scale production, SF9 insect cells were infected in 10 liter fermentors (Bioprocess group) (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% CHAPS. The homogenate was centrifuged at 10,000×G for 30 minutes, and the resultant supernatant was stored at −80° C. before being assayed by COX activity.

b. Assay for COX I and COX II Activity

Cox activity was assayed as PGE$_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The PGE$_2$ formed was measured by standard ELISA technology (Cayman Chemical). Results are shown in Table II.

TABLE II

| Examples | Murine COX I ID$_{50}$ μM | Murine COX II ID$_{50}$ μM |
|---|---|---|
| 1 | >100* | <.1 |
| 2 | 3.5 | <.1 |
| 3 | 100 | 1.5 |
| 4 | .3 | .8 |
| 5 | <3 | <.1 |
| 6 | <.3 | <.1 |
| 7 | <.1 | <.1 |
| 8 | >100 | 5.5 |
| 9 | >100 | 4.7 |
| 10 | >10 | <.1 |
| 11 | >100 | <.1 |
| 13 | >100* | 1.9 |
| 14 | >10 | .2 |
| 15 | 8.5 | <.1 |

*human COX I and COX II enzymes

Whole Blood Assay for Thromboxane B$_2$ Activity

Thromboxane B$_2$ (TXB$_2$) activity was assayed using an ELISA to detect the TXB$_2$ released. Various concentrations of compounds and standards were prepared by a set of serial dilutions (1:3) in a microtiter plate with ethanol. In U-bottom microtiter plates, 50 μl whole blood (green top heparin), 150 μl RPMI media (JRH Biosciences) and 5 μl compound solution were mixed and preincubated at 37° C. for fifteen minutes prior to the addition 4 μg of the calcium ionophore A23187. Any reaction between the compounds and the cells was stopped after ten minutes at 37° C. by centrifuging the cells at 2000 rpm for ten minutes at 4° C. and transferring 20 μl of the supernatant into 180 μl ELISA enzyme immuno assay buffer. The TXB$_2$ formed was measured by standard ELISA technology (Cayman Chemical). To washed and pre-coated (goat anti-rabbit IgG H&L) microtiter plates, was added 40 μl enzyme immune assay buffer, 10 μl diluted supernatants, 50 μl TXB$_2$ tracer and 50 μl TXB$_2$ antisera. After covered overnight incubation at room temperature, 300 μl Ellman reagent was added and incubated. The absorbance was read at 405 nm with a 650 nm reference. Results are shown in Table III.

TABLE III

| Examples | Thromboxane B$_2$ IC$_{50}$ μM |
|---|---|
| 1 | 21 |
| 2 | .4 |
| 4 | <.1 |
| 7 | <.1 |
| 10 | 7 |
| 11 | 7 |
| 14 | 27 |
| 15 | 28 |

The antiinflammatory agents of this invention can be administered to treat inflammation by any means that produces contact of the active agent with the agent's site of action in the body of a mammal, preferably human. These agents can be administered by any conventional means available for use in conjunction with pharmaceuticals, either as individual therapeutic agents or in a combination of therapeutic agents. The agents can be administered alone, but are generally administered with a pharmaceutical carrier select on the basis of the chosen route of administration, preferably oral, and standard pharmaceutical practice.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as lactose, sucrose, starch powder, cellulose esters of alkanoic acids, cellulose alkyl esters, talc, stearic acid, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents. Pharmaceutically acceptable carriers encompass all the foregoing and the like.

While the compounds of the invention can be administered as the sole active pharmaceutical agent, they can also be used in combination with one or more immunomodulators, antiviral agents or other antiinfective agents. For example, the compounds of the invention can be administered in combination with antihistamines or with other such agents known heretofore to be effective in combination with antiinflammatory agents. When administered as a combination, the therapeutic agents can be formulated as separate compositions which are given at the same time or different times, or the therapeutic agents can be given as a single composition.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

Although this invention has been described with respect to specific embodiments, the details of these embodiments are not to be construed as limitations.

What is claimed is:

1. A compound of Formula I:

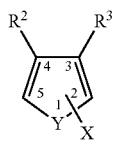

I wherein Y is S;
wherein X is one or more substituents selected from
a) hydrido, halo, cyano, nitro, hydroxy, acyl, lower alkyl substituted at a substitutable position with a substituent selected from halo, hydroxyl, amino, acylamino, lower alkylamino, lower alkyl(acyl)amino, acyl, aryl optionally substituted with hydroxyl, a heterocyclic group, hydroxyimine and lower alkoxyimino, lower alkenyl optionally substituted at a substitutable position with cyano, amino optionally substituted at a substitutable position with a radical selected from acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (esterified carboxy)lower alkyl, N-containing heterocyclicsulfonyl, a heterocyclic group optionally substituted at a substitutable position with a substituent selected from the group consisting of hydroxyl, oxo, amino and lower alkylamino,
b) $S(O)_nR^5$, wherein $R^5$ is $C_1$–$C_7$ alkyl optionally substituted at a substitutable position with fluoro, and n is 0, 1 or 2,
c) $C(R^6)(OR^8)(R^7)$ wherein $R^6$ and $R^7$ independently are selected from $CF_3$, $CF_2H$, $CFCl_2$, $CF_2Cl$, $CClFH$, $CCl_2F$, $CF_3CF_2$ and $C_1$–$C_2$ alkyl, and wherein $R^8$ is selected from hydrido, $C_1$–$C_4$ alkyl, $(C_1$–$C_3$ alkyl)$C(O)$ and $CO_2R^9$, wherein $R^9$ is $C_1$–$C_4$ alkyl,
d) $C(O)ZR^4$, wherein Z is O, N, or S, and $R^4$ is selected from hydrido, $C_1$–$C_6$ alkyl and aryl, and when Z is N then R4 is independently taken twice, and
e) $C(R^9)(NHR^{11})(R^{10})$, wherein $R^9$ and $R^{10}$ are independently selected from $CF_3$, $CF_2H$, $CFCl_2$, $CF_2Cl$, $CClFH$ and $CCl_2H$, and $R^{11}$ is selected from hydrido and $C_1$–$C_3$ alkyl; and wherein $R^2$ and $R^3$ are independently selected from aryl or heteroaryl, wherein the aryl or heteroaryl radical is optionally substituted at a substitutable position with a radical selected from halo, lower alkyl, lower alkoxy, lower alkylthio, lower alkylsulfinyl, lower alkylsulfonyl, nitro, amide, amino, lower alkylamino, sulfamyl and lower alkylsulfonylamino;
provided that at least one of $R^2$ or $R^3$ is substituted with lower alkylsulfonyl or sulfamyl;
or a pharmaceutically-acceptable salt thereof.

2. A compound of claim 1 wherein X is $S(O)_nR^5$, wherein $R^5$ is $C_1$–$C_6$ alkyl optionally substituted at a substitutable position with fluoro, and n is 0, 1 or 2; or a pharmaceutically-acceptable salt thereof.

3. A compound of claim 1 wherein X is $C(R^6)(OR^8)(R^7)$, wherein $R^6$ and $R^7$ independently are selected from the group consisting of $CF_3$, $CF_2H$, $CFCl_2$, $CF_2Cl$, $CClFH$, $CCl_2F$, $CF_3CF_2$ and $C_1$–$C_2$ alkyl; wherein $R^8$ is selected from the group consisting of hydrido, $C_1$–$C_4$ alkyl, $(C_1$–$C_3$ alkyl)$C(O)$ and $CO_2R^9$; and wherein $R^9$ is $C_1$–$C_4$ alkyl; or a pharmaceutically acceptable salt thereof.

4. A compound of claim 1 wherein X is $C(R^9)(NHR^{11})(R^{10})$, wherein $R^9$ and $R^{10}$ are independently selected from the group consisting of $CF_3$, $CF_2H$, $CFCl_2$, $CF_2Cl$, $CClFH$ and $CCl_2H$, and $R^{11}$ is selected from the group consisting of hydrido, $C_1$–$C_3$ alkyl; or a pharmaceutically acceptable salt thereof.

5. A compound of claim 1 wherein $R^2$ and $R^3$ are independently selected from aryl and heteroaryl, wherein the aryl or heteroaryl radical is optionally substituted at a substitutable position with a member selected from the group consisting of halo, lower alkyl, lower alkoxy, lower alkylthio, lower alkylsulfinyl, lower alkylsulfonyl, nitro, amino, lower alkylamino, sulfamyl and lower alkylsulfonylamino; or a pharmaceutically-acceptable thereof, provided that at least one of $R^2$ or $R^3$ is substituted with lower alkylsulfonyl or sulfamyl.

6. The compound of claim 1 wherein X is one or two substituents selected from the group consisting of hydrido, halo, cyano, nitro, hydroxyl, acyl, lower alkyl substituted at a substitutable position with a substituent selected from the group consisting of halo, hydroxyl, amino, acylamino, lower alkylamino, lower alkyl(acyl)amino, and acyl, aryl optionally substituted with hydroxyl, a heterocyclic group, hydroxyimino and lower alkoxyimino, lower alkenyl optionally substituted at a substitutable position with cyano, amino optionally substituted at a substitutable position with a radical selected from the group consisting of acyl and lower alkylsulfonyl, sulfo, sulfamoyl optionally substituted with a substituent selected from the group consisting of lower alkyl, halo(lower)alkyl, aryl, hydroxyl, lower alkylamino (lower)alkyl, a heterocyclic group and (esterified carboxy) lower alkyl, N-containing heterocyclicsulfonyl, a heterocyclic group optionally substituted at a substitutable position with a substituent selected from the group consisting of hydroxyl, oxo, amino and lower alkylaxnino; and wherein $R^2$ and $R^3$ are independently selected from aryl and heteroaryl, wherein the aryl or heteroaryl radical is optionally substituted at a substitutable position with a radical selected from the group consisting of halo, lower alkyl, lower alkoxy, lower alkylthia, lower alkylsulfinyl, lower alkylsulfonyl, nitro, amino, amide, lower alkylamino, sulfamyl and lower alkylsulfonylamino; or a pharmaceutically-acceptable salt thereof,
provided that at least one of $R^2$ or $R^3$ is substituted with lower alkylsulfonyl or sulfamyl.

7. The compound of claim 1 wherein Y is S; wherein X is one or two substituents selected from the group consisting of hydrido, halo, cyano, nitro, hydroxyl, carboxyl, lower alkoxycarbonyl, lower alkyl substituted at a substitutable position with a substituent selected from the group consisting of halo, hydroxyl, amino, acylaniino, lower alkylamino, lower alkyl(acyl)amino, lower alkoxycarbonyl, carboxy, a heterocyclic group, hydroxyimino and lower alkoxyimino, lower alkenyl optionally substituted at a substitutable position with cyano, amino optionally substituted at a substitutable position with a radical selected from the group consisting of acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (alkoxycarbonyl)lower alkyl, N-containing heterocycliesulfonyl, a heterocyclic group optionally substituted at a substitutable position with a substituent selected from the group consisting of hydroxyl, oxo, amino and lower alkylamino; and wherein $R^2$ and $R^3$ are independently selected from aryl and heteroaryl, wherein the aryl or heteroaryl radical is optionally substituted at a substitutable position with a radical selected from the group consisting of halo, lower alkyl, lower alkoxy, lower alkylthio, lower alkylsulfinyl, lower alkylsulfonyl, nitro, amino, amide, lower alkylamino, sulfamyl and lower ailcylsulfonylamino; or a pharmaceutically-acceptable salt thereof, provided that at least one of $R^2$ or $R^3$ is substituted with lower alkylsulfonyl or sulfamyl.

8. The compound of claim 1 wherein Y is $NR^1$, wherein X is one or two substituents selected from the group consisting of hydrido, halo, cyano, nitro, hydroxyl, carboxyl, lower alkoxycarbonyl, lower alkyl substituted at a substitutable position with a substituent selected from the group consisting of halo, hydroxyl, amino, acylamino, lower alkylamino, lower alkyl(acyl)amino, lower alkoxycarbonyl, carboxy, a heterocyclic group, hydroxyimino and lower alkoxyimino, lower alkenyl optionally substituted at a substitutable position with cyano, amino optionally substituted at a substitutable position with a radical selected from the group consisting of acyl and lower alkylsulfonyl, sulfo, sulfamoyl optionally substituted with a substituent selected from the group consisting of lower alkyl, halo(lower)alkyl, aryl, hydroxyl, lower alkylamino(lower)alkyl, a heterocyclic group and (alkoxycarbonyl)lower alkyl, N-containing heterocyclicsulfonyl, a heterocyclic group optionally substituted at a substitutable position with a substituent selected from the group consisting of hydroxyl, oxo, amino and lower alkylamino; and wherein $R^2$ and $R^3$ are independently selected from aryl and heteroaryl, wherein the aryl or heteroaryl radical is optionally substituted at a substitutable position with a radical selected from the group consisting of halo, lower alkyl, lower alkoxy, lower alkylthio, lower alkylsulfinyl, lower alkylsulfonyl, nitro, amino, amide, lower alkylamino, sulfamyl and lower alkylsulfonylamino; or a pharmaceutically-acceptable salt thereof, provided that at least one of $R^2$ or $R^3$ is substituted with lower alkylsulfonyl or sulfamyl.

9. The compound of claim 1 wherein X is one or two substituents selected from the group consisting of hydrido, fluoro, chloro, bromo and iodo; or a pharmaceutically-acceptable salt thereof.

10. A compound of Formula II:

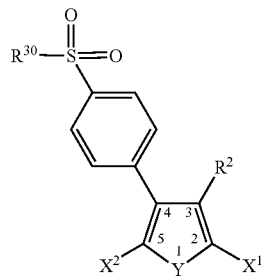

wherein Y is S;
wherein $X^1$ and $X^2$ are independently selected from hydrido, halo, lower alkoxycarbonyl and carboxyl;
wherein $R^2$ is selected from the group consisting of aryl and heteroaryl; wherein $R^2$ is optionally substituted at a substitutable position with a radical selected from halo, lower alkoxy and lower alkyl; and
wherein $R^{30}$ is selected from amino and lower alkyl;
or a pharmaceutically-acceptable salt thereof.

11. The compound of claim 10; wherein $R^2$ is selected from the group consisting of phenyl, naphthyl, biphenyl, and pyridyl; wherein $R^2$ is optionally substituted at a substitutable position with a radical selected from the group consisting of halo, lower alkoxy and lower alkyl; and
wherein $R^{30}$ is selected from the group consisting of amino and $C_1$–$C_3$ alkyl;
or a pharmaceutically-acceptable salt thereof.

12. The compound of claim 11, wherein $X^1$ and $X^2$ are independently selected from the group consisting of hydrido, fluoro, chloro, bromo, iodo, methoxycarbonyl, ethoxycarbonyl and carboxyl;
wherein $R^2$ is phenyl or pyridyl; wherein $R^2$ is optionally substituted at a substitutable position with a radical selected from the group consisting of fluoro, chloro, bromo, iodo, methoxy, ethoxy, methyl and ethyl; and
wherein $R^{30}$ is amino or methyl;
or a pharmaceutically-acceptable salt thereof.

13. The compound of claim 12 selected from the group consisting of:
4-(4-methylsulfonylphenyl)-3-(4-fluorophenyl)thiophene;
4-(4-methylsulfonylphenyl)-3-(4-fluorophenyl)-2,5-dibromothiophene;
4-(4-methylsulfonylphenyl)-3-(4-fluorophenyl)-2-bromothiophene;
ethyl[3-(4-methylsulfonylphenyl)-4-(4-fluorophenyl)thien-2-yl]carboxylate;
2-ethoxycarbonyl-4-(4-fluorophenyl)-3-(4-methylsulfonylphenyl)thienyl-5-carboxylic acid;
4-(4-fluorophenyl)-3-(4-methylsulfonylphenyl)thienyl-2,5-dicarboxylic acid;
4-(4-methylsulfonylphenyl)-3-(4-methoxyphenyl)thiophene;
4-(4-methylsulfonylphenyl)-3-(4-methoxyphenyl)-2-bromothiophene;
3-(4-methylsulfonylphenyl)-4-phenyl-thiophene;
3-(4-methylsulfonylphenyl)-4-(4-methylphenyl)thiophene;
3-(4-methylsulfonylphenyl)-4-(2-methyl-4-fluorophenyl)thiophene;

2-fluoro-5-[3-(4-methylsulfonylphenyl)thien-4-yl]pyridine;

4-[4-(4-fluorophenyl)thien-3-yl]benzenesulfonamide;

4-[3-(4-fluorophenyl)-2,5-dibromo-thien-4-yl]benzenesulfonamide; and

4-[3-(4-fluorophenyl)-2-bromo-thien-4-yl]benzenesulfonamide; and their pharmaceutically acceptable salts.

14. A pharmaceutical composition comprising a therapeutically-effective amount of an antiinflammatory compound, said compound selected from a compound of claim 1, or a pharmaceutically-acceptable salt thereof.

15. A pharmaceutical composition comprising a therapeutically-effective amount of an antiinflammatory compound, said compound selected from a compound of claim 10; or a pharmaceutically-acceptable salt thereof.

16. A pharmaceutical composition comprising a therapeutically-effective amount of an antiinflammatory compound, said compound selected from a compound of claim 11; or a pharmaceutically-acceptable salt thereof.

17. A pharmaceutical composition comprising a therapeutically-effective amount of an antiinflammatory compound, said compound selected from a compound of claim 12; or a pharmaceutically-acceptable salt thereof.

18. A pharmaceutical composition comprising a therapeutically-effective amount of an antiinflammatory compound, said compound selected from a compound of claim 13; or a pharmaceutically-acceptable salt thereof.

19. The composition of claim 18 wherein the compound is 4-[4-(4-fluorophenyl)thien-3-yl]benzenesulfonamide; or a pharmaceutically acceptable salt thereof.

20. The composition of claim 18 wherein the compound is 4-[3-(4-fluorophenyl)-2-bromo-thien-4-yl]benzenesulfonamide; or a pharmaceutically acceptable salt thereof.

21. A method for treating inflammation or an inflammation-associated disorder comprising administering a therapeutically effective amount of a compound of claim 1 to a subject in need thereof.

22. A method for treating inflammation or an inflammation-associated disorder comprising administering a therapeutically effective amount of a compound of claim 10 to a subject in need thereof.

23. A method for treating inflammation or an inflammation-associated disorder comprising administering a therapeutically effective amount of a compound of claim 11 to a subject in need thereof.

24. A method for treating inflammation or an inflammation-associated disorder comprising administering a therapeutically effective amount of a compound of claim 12 to a subject in need thereof.

25. A method for treating inflammation or an inflammation-associated disorder comprising administering a therapeutically effective amount of a compound of claim 13 to a subject in need thereof.

26. The method of claim 25, wherein said compound is 4-4-(4-fluorophenyl)thien-3-yl]benzenesulfonamide; or a pharmaceutically acceptable salt thereof.

27. The method of claim 25, wherein said compound is 4-3-(4-fluorophenyl)-2-bromo-thien-4-yl]benzenesulfonamide; or a pharmaceutically acceptable salt thereof.

28. The method of claim 21 for treating inflammation.

29. The method of claim 21 for treating an inflammation-associated disorder.

30. The method of claim 29 wherein the inflammation-associated disorder is arthritis.

31. The method of claim 29 wherein the inflammation-associated disorder is pain.

32. The method of claim 29 wherein the inflammation-associated disorder is fever.

* * * * *